United States Patent [19]

Squires et al.

[11] 4,216,779

[45] Aug. 12, 1980

[54] BLOOD PRESSURE MONITORING SYSTEM

[75] Inventors: W. David Squires; Donald L. Anderson, both of Huntington Beach; Isaac R. Cherry, Mission Viejo, all of Calif.

[73] Assignee: Del Mar Avionics, Irvine, Calif.

[21] Appl. No.: 796,893

[22] Filed: May 16, 1977

[51] Int. Cl.$^2$ .............................................. A61B 5/02
[52] U.S. Cl. .................................. 128/682; 128/700; 128/708; 128/710; 128/900; 346/33 ME; 360/6; 360/18
[58] Field of Search .................... 128/2.05 A, 2.05 M, 128/2.05 R, 2.06 A, 2.06 G, 2.05 Q, 2.1 A, 672, 679–683, 700, 708, 710; 346/33 M, 33 ME; 360/6, 18, 27; 364/415, 417

[56] References Cited

U.S. PATENT DOCUMENTS

| | | | |
|---|---|---|---|
| 3,087,488 | 4/1963 | Streimer | 346/33 ME |
| 3,508,537 | 4/1970 | Kahn et al. | 128/2.05 A |
| 3,552,381 | 1/1971 | Burns et al. | 128/2.05 A |
| 3,552,383 | 1/1971 | Krueger | 128/2.05 A |
| 3,654,915 | 4/1972 | Sanctuary | 128/2.05 M |
| 3,814,083 | 6/1974 | Fletcher et al. | 128/683 |
| 3,838,445 | 9/1974 | Copp et al. | 360/18 |
| 3,903,872 | 9/1975 | Link | 128/2.05 A |
| 3,913,567 | 10/1975 | Streckmann | 128/2.06 G |
| 3,934,267 | 1/1976 | Kosaka et al. | 128/2.06 G X |
| 3,978,848 | 7/1976 | Yen et al. | 128/2.05 M |
| 4,033,336 | 7/1977 | Murawski et al. | 128/2.05 R |
| 4,058,117 | 11/1977 | Kaspari et al. | 128/2.05 A |
| 4,069,815 | 1/1978 | Lee | 128/2.05 A |
| 4,073,011 | 2/1978 | Cherry et al. | 128/2.06 A X |
| 4,116,230 | 9/1978 | Gorelick | 128/2.05 M |
| 4,123,785 | 10/1978 | Cherry et al. | 360/4 |

FOREIGN PATENT DOCUMENTS 1391948  6/1972  United Kingdom ............... 346/33 ME

OTHER PUBLICATIONS

McKinnon, J. B. "A Miniature 4-Channel Cassette Recorder for Physiological and Other Variables", 2nd Int. Symp. Biotelemetry, Davos, Switz., May 20–24, 1974, pp. 67–70.
"Live Recorder for ECG Studies of the Heart", Honeywell Corp., Biomed Engr. vol. 7, No. 3 (Apr. 1972).
Beaumont, E. "Blood Pressure Equipment", Nursing, Jan. 1975, pp. 56–62.
Fryer, T. B. et al., "A Multi-Channel Implant Telemetry System for Cardiovascular Flow, Pressure, and ECG Measurement", pp. 40–42.
Antila, K. et al., "Performance of a Special Purpose Computerized Heart-Rate Monitoring System & Evaluation of Measurement Accuracy", Proc. of 1st Natnl. Meeting on Biophys. & Biotech. in Finland, Helsinki, Jan. 4–5, 1973, pp. 162–164.
Graham, M., "µP Checks EKG and Pressure", Electronics Design, Sep. 13, 1976, p. 28.
Randall, M. J. "Computer Automation of BP Measurements", IEEE Proc. vol. 63, No. 10, pp. 1399–1403, Oct. 1975.
Fryer, T. B. et al., "A Multi-Channel Biotelemetry Transmitter Utilizing a PCM Subcarrier", 2nd Int. Symp. Biotelemetry, Davos, Switz., May 20–24, 1974, pp. 202–204.

Primary Examiner—Robert W. Michell
Assistant Examiner—Francis J. Jaworski
Attorney, Agent, or Firm—Smyth, Pavitt, Siegemund, Jones & Martella

[57] ABSTRACT

Apparatus is disclosed for long-term ambulatory monitoring of blood pressure by an auscultation method, employing a pressurizable cuff and requiring no intervention by the patient. Heartbeats are sensed by ECG electrodes, and a microphone is used to sense the Korotkow sounds as the pressure in the cuff is varied. The presence or absence of a Korotkow sound within a preset interval following each heartbeat is used in determining when the cuff pressure equals the systolic and diastolic pressures. Those pressures are determined in each cycle of operation and are recorded on a continuously-running portable tape recorder, along with the ECG signals. In each cycle of operation, the initial pressure to which the cuff is inflated is based on the systolic pressure measured in the immediately preceding cycle. The pressure in the inflated cuff is thereafter stepped downward in small discrete decrements triggered by successive heartbeats during the measurement phase of each cycle. After both the systolic and diastolic pressures have been determined, the remaining cuff pressure is vented through the same valve that was used to produce the stepwise pressure reduction. After a number of cycles of operation, the magnetic tape is removed from the portable recorder and inserted into an analyzer for high-speed playback and automated plotting of the heart rate and accompanying blood pressure readings on a common chart.

32 Claims, 19 Drawing Figures

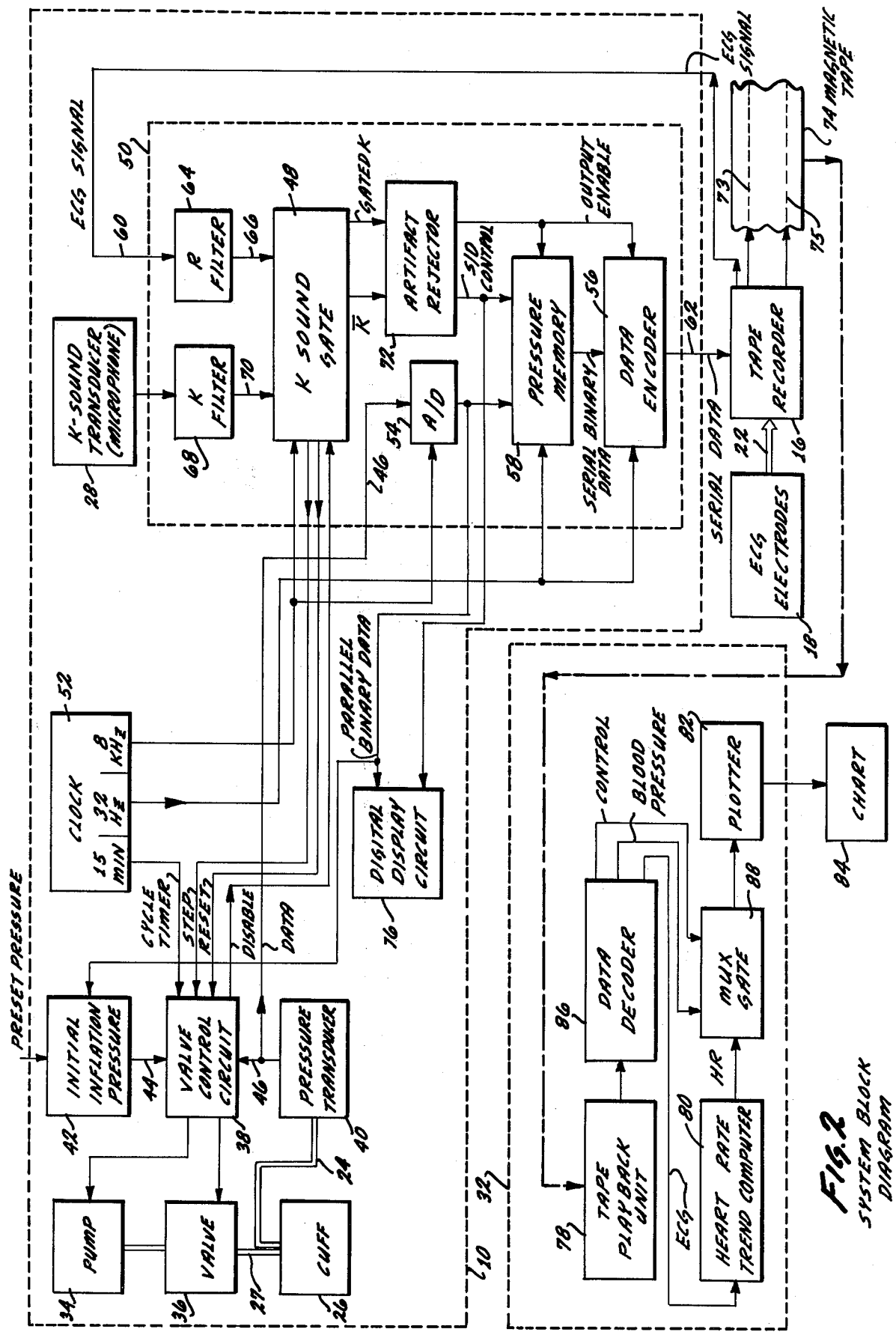

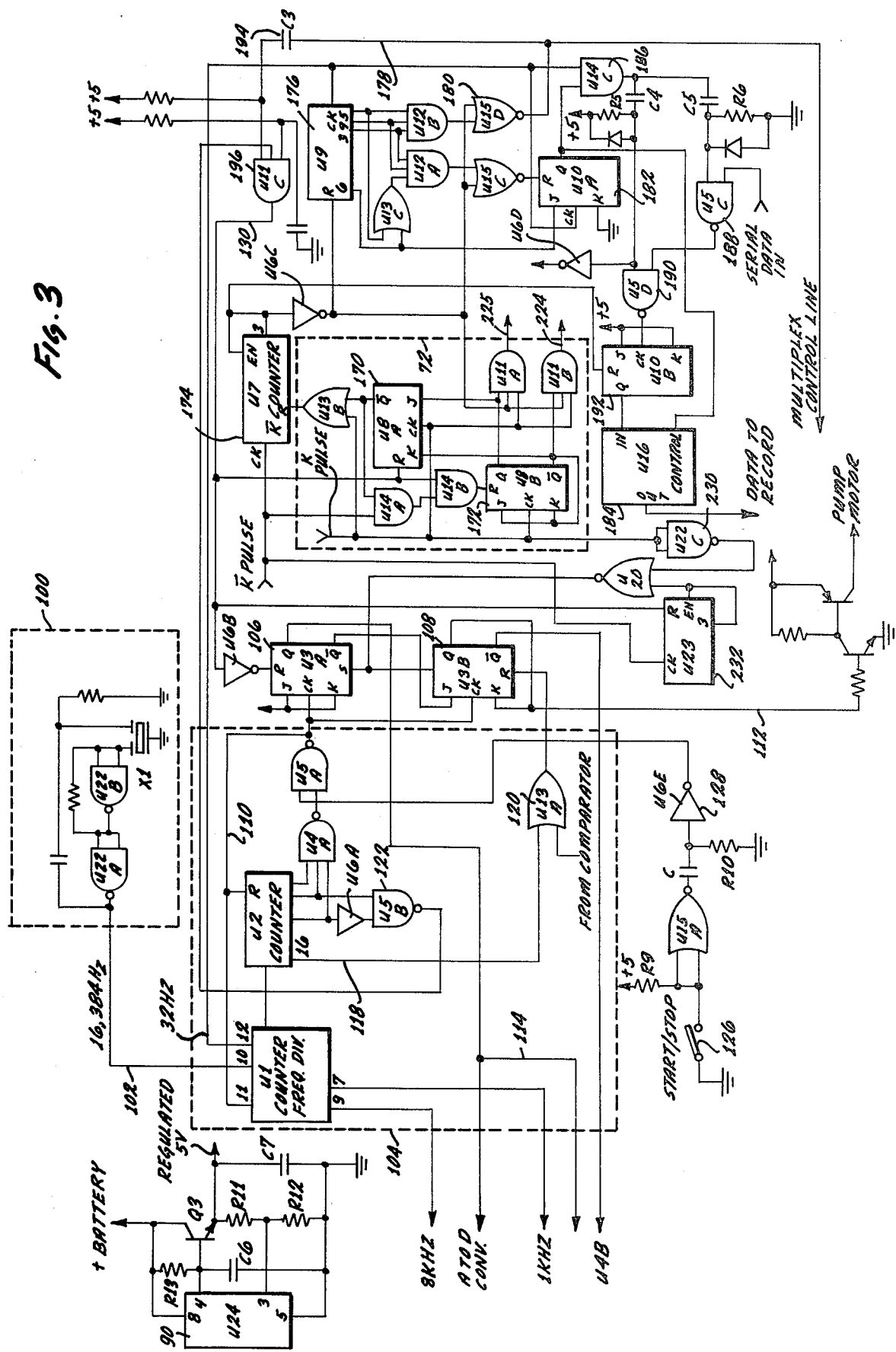

BLOOD PRESSURE MONITORING SYSTEM

BACKGROUND OF THE INVENTION

1. Field of the Invention

The present invention provides apparatus for measuring and recording systolic and diastolic blood pressure by an indirect auscultation method, and particularly provides for long-term ambulatory monitoring of blood pressure by recording it on tape and subsequently playing it back from the tape at a higher speed for analysis and plotting.

2. The Prior Art

The auscultation method dates from the discovery in 1905 by Korotkow that sounds audible on a stethoscope are produced when the flow of blood through a brachial artery is partially obstructed. According to that method, an inflatable cuff is placed on the arm and inflated to a pressure greater than the systolic blood pressure of the patient. Thereafter, the pressure in the cuff is gradually reduced and at first no sounds are heard. When the decreasing pressure in the cuff has fallen below the systolic pressure, Korotkow sounds are produced, one such sound being produced for each beat of the heart. As the cuff pressure decreases further, approaching the diastolic pressure, the Korotkow sounds continue to be heard, but as the cuff pressure falls below the diastolic blood pressure, the Korotkow sounds are heard no more, being inaudible for cuff pressures less than the diastolic blood pressure.

Considerable effort has been applied to automate the auscultatory method of measuring blood pressure, so that measurements can be performed by relatively unskilled personnel, or automatically, once the apparatus has been set up. A persistent problem has been the discrimination of the Korotkow sounds from other acoustical signals referred to in the art as artifacts. These artifacts, or false signals, can be generated by muscular movements of the patient among other things, and if they are mistaken for true Korotkow sounds, they will result in erroneous identification of the systolic or diastolic blood pressure. Thus, the artifact problem is especially critical when the device is intended for ambulatory monitoring of blood pressure, particularly in the case of children or disturbed persons.

From the standpoint of the comfort and safety of the patient, it is desirable that the duration of the measuring period as well as the cuff pressure be minimized. From the standpoint of the doctor, it is desirable that the results of the monitoring be available promptly and with a minimum of analysis, yet be in a meaningful form. These desiderata have been given due consideration in the present invention, which can best be appreciated in view of the prior art which will now be described:

In U.S. Pat. No. 2,827,040, Gilford discloses an automatic sphygmomanometer. Gilford uses a thermistor pressure impulse detector to sense the heart beat. The output of the pressure impulse detector is used to establish a time interval within which the K-sounds must occur to be regarded as true K-sounds. Gilford also requires two successive K-sound detections before a recording is made. Pressure is measured while the cuff pressure is increased, so that the diastolic measurement is made first and the systolic measurement is made last.

In U.S. Pat. No. 3,051,165, Kompelien uses an optical transducer applied to the patient's earlobe to sense variations in the opacity of the ear tissue to generate a signal from which the blood pressure can be detected.

In U.S. Pat. Nos. 3,996,926 and 3,893,452, Birnbaum discloses an invasive (catheter) blood pressure monitoring system and display.

In U.S. Pat. No. 3,137,292, Richter et al. determine the cuff pressure at the first and last K-sound in an automatic measuring cycle.

In U.S. Pat. No. 3,326,230, Follett generates narrow pressure calibration pulses as the steadily decreasing pressure drops below successive discrete pressure levels. These calibration pulses are superimposed on the K-sound signal and the combined signal is plotted. The systolic and diastolic blood pressures are then determined by inspection.

In U.S. Pat. Nos. 3,202,148 and 3,319,623, London shows apparatus for monitoring blood pressure using a column of indicator lights corresponding to successive pressure levels. As the cuff pressure decreases, a light is lit corresponding to the instantaneous pressure if a K-sound is present. At the end of a measuring cycle, the column will include normally several lights at the top or high pressure end which have not been lit followed by a series of lights which have been activated and followed by a few more lights which have not been lit. The uppermost and lowermost lights which have been activated indicate the systolic and diastolic pressure intervals respectively. In one version of the London apparatus, a paper chart plot is prepared automatically to show the systolic and diastolic pressures versus time.

In U.S. Pat. No. 3,450,131, Vogt uses a 1,000 Hz filter to detect artifact signals which are then used to establish discrimination gates for the K-signals.

In U.S. Pat. No. 3,654,915, assigned to the assignee of the present invention, Sanctuary shows an apparatus for automatically measuring and indicating blood pressure. The apparatus incorporates a number of advantageous safety features. The signal processing to eliminate artifacts includes the elimination of K-sounds which are neither preceded nor succeeded by another K-sound. Pressure is sensed by a mercury column manometer having a plurality of feeler contacts. The measurements are indicated by a column of lamps and can be recorded by a plotter. During each cycle of operation, the cuff is initially pressurized to a chosen level and thereafter the pressure is reduced through a linear cuff leak valve which is a distinct part from the dump valve used to vent the cuff pressure at the end of each measuring cycle.

The present invention differs from the invention of Sanctuary in a number of ways, which will become clearer below, but which will be enumerated here for convenience. The Sanctuary invention was only semiportable, was power line operated and was not intended for long-term monitoring. In contrast, the present invention is truly portable and is intended for ambulatory recording during intervals up to twenty-six hours or more.

The Sanctuary invention included a column of lamps to display the successive measurements, although a paper tape record could also be provided. In contrast, the present invention has available an instantaneous digital display of each blood pressure result. In the present invention, the measurements are recorded on a magnetic tape and later replayed at high speed for plotting.

The Sanctuary invention used a mercury column manometer while the present invention uses a pressure transducer that operates on a different principle.

In the present invention, the same valve is used for bleeding the cuff and for quickly dumping the cuff pressure at the conclusion of the measuring cycle. In contrast, in the Sanctuary invention separate dump and bleeder valves are used.

More importantly, the present invention is distinguished from all of the above-mentioned prior art inventions, including the Sanctuary invention, in the following ways.

Firstly, in the present invention the blood pressure measurements are recorded on a magnetic tape along with simultaneously-made ECG (electrocardiogram) signals. This assures maintenance of the correlation of these signals with the blood pressure measurements and facilitates later analysis.

Secondly, in the present invention, the cuff pressure is stepped downward in discrete decrements triggered by successive ECG heartbeats or at discrete time intervals in the absence of ECG heartbeat signals. This has the advantage of speeding up the blood pressure measuring process over prior art methods. Some of the prior art inventions use cuff pressure bleeds which are linear or exponentially decreasing in time in an attempt to leak at a rate compatible with the slowest heart rate expected. Therefore, the leak rate is slow. The common method practiced by most physicians with simple apparatus, manually sets a fixed leak which slows down and uses more time per unit of pressure decrease as the pressure becomes lower.

Thirdly, in the present invention the initial pressure to which the cuff is pumped during the second and successive cycles of operation is based on the systolic blood pressure measured in the immediately preceding cycle. This speeds up the measuring process and also reduces patient discomfort by avoiding unnecessary pressure levels.

Fourthly, the present system makes use of a common automatic plotting mechanism to mark the systolic and diastolic blood pressure readings at set intervals on a heart rate chart to facilitate recognition of trends.

Fifthly, in the present invention, the cuff pressure transducer is located inside the housing of the blood pressure measuring apparatus and is connected to the cuff by an air hose which is separate from the air hose used for inflating and deflating the cuff. This expedient is an improvement over connecting the pressure transducer hose to the inflation hose at a point within the housing near the valve, because the cuff serves as an air ballast to substantially isolate the pressure transducer from pressure transients generated by the opening and closing of the valve.

SUMMARY OF THE INVENTION

The present invention is a specialized form of blood pressure measuring apparatus which fills the need for a long-term ambulatory simultaneous measurement of blood pressure and ECG signals. The system uses a combination of proven elements integrated into a comprehensive system for achieving this result. For convenience, the Blood Pressure Monitoring System of the present invention will be referred to below as the B.P.M. System.

The ECG electrical signals are picked up from the patient's body by ECG electrodes. These electrical signals, along with the blood pressure readings to be described, are recorded on a portable magnetic recorder for later playback and plotting. In a preferred embodiment, the recorder and playback unit are similar to those described in U.S. patent application Ser. No. 717,651 filed Aug. 25, 1976 by Cherry and Anderson, and assigned to the assignee of the present invention, now U.S. Pat. No. Re 29,921, reissued Feb. 27, 1979.

In the present invention, blood pressure is measured by the auscultatory method in which a pressurizable cuff is fitted to the arm of the patient and inflated to varying pressures. In a preferred embodiment of the present invention, an electrically-driven air pump is used as the source of pressure, although in other embodiments pressure could be supplied from a tank of compressed air or hydraulic pressure could be employed.

A three-way valve is connected between the cuff and the pump or other source of pressure. In a preferred embodiment, the valve has a core which is movable at very high speed to either of two positions by selective application of electrical signals. Thus, the valve can be either fully open or fully closed or in transition therebetween. When the valve is not energized the core of the valve is positioned so as to vent the cuff to the atmosphere. In response to an applied electrical signal, the core of the valve is rapidly shifted so as to close the vent and connect the cuff to the pump. The valve thus provides a fail-safe feature in the present invention, because if the electrical power is disabled, the valve will revert, under the action of a return spring or like means, to the de-energized position thereby venting the cuff and preventing it from being pressurized for excessive intervals.

In a preferred embodiment of the present invention, a pump supplies air to inflate the cuff, and the pump is of a type which, after being turned off, effectively seals the conduit by which it is connected to the valve.

The circuit which supplies the electrical signals controlling the operation of the valve includes additional safety features in the form of timers. One of these timers is set to de-energize the valve a predetermined interval, about two minutes, after the beginning of each cycle of operation, thereby preventing excessively prolonged application of cuff pressure. Another timer de-energizes the valve if the pump remains on for an excessive time, thereby preventing excessive cuff pressures from being attained.

Still another timer is reset with each K-sound that is sensed so that it never has a chance to run down as long as the succession of K-sounds is unbroken. Once the K-sounds have ceased, indicating that the diastolic pressure measurement has been completed, the timer concludes its rundown and de-energizes the valve, thereby relieving the cuff pressure a couple of seconds after the diastolic pressure measurement has been completed.

An initial peak inflation pressure representing the maximum desired cuff inflation pressure is manually preset at the beginning of a series of measurement cycles. Measurement cycles are repeated as desired to suit the need to find blood pressure on a patient. The time of day for instigation of an automatic measurement cycle may be set on a clock or interval timer as explained later. Alternatively, measurement cycles may be initiated manually by the patient. In the pumping phase of the first measurement cycle, the valve control circuitry will continue to energize the valve, permitting inflation of the cuff, until the sensed cuff pressure equals the preset initial inflation pressure. Thereafter, the valve control circuitry acts to bleed down the pressure at a controlled rate to explore and obtain K-sounds representing pressure valves associated with systolic and diastolic blood pressure.

In the present invention, the cuff pressure is always sensed by a pressure transducer which preferably is not a mercury manometer. After the pressure transducer senses that the desired initial cuff inflation pressure has been reached, in the present invention the cuff pressure is reduced in a variably-time-controlled stepwise manner through a series of individual constant pressure decrements paced by successive heartbeats. This is accomplished, in a preferred embodiment, by sensing the R-peak of the ECG signal and generating from it a stepping signal which is applied to the valve control circuitry for intermittently de-energizing the valve, thereby reducing the cuff pressure by a step of predetermined magnitude with each heartbeat.

The Korotkow sounds (herein referred to as K-sounds) are detected by a transducer, which in a preferred embodiment is a microphone located on the brachial artery of the patient's arm under the pressure cuff. Assuming the initial inflation pressure in a cycle of operation is considerably greater than the systolic pressure, no K-sounds will be heard initially. As the cuff pressure is reduced, a point is reached at which the first K-sound is sensed. K-sounds continue to be sensed after each heartbeat until the cuff pressure has decreased sufficiently to equal the diastolic pressure. When the cuff pressure is less than the diastolic pressure, the K-sounds cease and are not heard for the remainder of the cycle of operation.

After the initial inflation to the preset peak inflation pressure, the system determines the time of occurrence of each heartbeat by sensing the occurrence of the associated R-wave in the ECG signal. If a K-sound occurs within a prescribed time interval or gate of the occurrence of the R-wave, the system determines that the cuff pressure is within the range of pressures for which K-sounds are produced.

The system includes provision for the situation in which R-waves are not generated by the patient or, if generated, are not sufficiently strong or well-defined to be detected by the system. In this situation, the system, upon not receiving any R-waves after the cuff has been pressurized, switches to a different ungated mode of operation. In the ungated mode of operation, the system sets up successive two-second time intervals, and if a K-sound occurs within an interval, the system determines that the cuff pressure is within the range of pressures for which K-sounds are produced.

Cuff pressure is sensed continually, but the system stores the instantaneous value of cuff pressure prevailing at the time of occurrence of a K-sound. As will be seen below, it is not necessary to store the entire succession of pressure values; only the most recent pressure value is stored. If the system determines that the most recent pressure value was associated with the first K-sound, the pressure value is transmitted as the systolic pressure. If the system determines that the most recent pressure value was associated with the last K-sound, the pressure value is transmitted as the diastolic pressure.

In the present invention, a discrimination circuit is employed to identify the first and last K-sounds. Following each peak on the ECG signal, the discrimination circuit sets up a delayed time interval and an open gate during which the K-sound would normally be expected to occur, if it is going to occur. This gating technique is advantageous in reducing false K-sound identifications resulting from artifact noise. For each heartbeat, the discrimination circuit opens the gate and generates a "K signal" if an actual K-sound follows the heartbeat within the gate interval, or generates an electronically produced signal, henceforth called a K-bar or $\overline{K}$ signal if no K-sound was sensed within the gate interval.

The discrimination circuit stores the cuff pressure associated with each heartbeat, although as will be seen, it is only necessary to store a few pressure readings at any one time. In a preferred embodiment, the discrimination circuit is responsive to the generation, following successive heartbeats, of three $\overline{K}$ signals followed by two K signals to identify the pressure associated with the first K signal as the systolic pressure. Likewise, the discrimination circuit is responsive to the generation, following successive heartbeats, of two K signals followed by three $\overline{K}$ signals to identify the pressure associated with the last K signal as the diastolic pressure. In a preferred embodiment of the present invention, all pressure readings are converted to digital form for ease of storage, retrieval, and subsequent recording.

The peak inflation pressure for the second and subsequent measurement cycles is determined by the valve control circuitry. Each time a measured pressure value is stored, the system generates and stores an augmented pressure value, equal to the measured pressure value plus a constant predetermined increment, such as 20 mmHg.

If a K-sound is heard before the third heartbeat (or six seconds in the ungated mode) after the peak inflation pressure has been reached, it signifies that the peak inflation pressure was either within the Korotkow pressure range or unacceptably close to it. In this case, the pressure associated with the K-sound cannot be established as the systolic pressure. Therefore, the cuff is immediately pumped up to the augmented value of the pressure sensed at the occurrence of the K-sound, and the system attempts again to establish a systolic pressure measurement. If, for example, the initial peak pressure were 160 mmHg, the second inflation might result in a peak pressure of 174 mmHg.

If the first K-sound is not heard until after the third heartbeat (or six seconds in the ungated mode) following the initial inflation, it signifies that the peak inflation pressure was excessive, unnecessarily prolonging the measurement. In this case, the instantaneous pressure sensed at the occurrence of the first K-sound is stored and the measurement is allowed to proceed. At the end of the measurement, after both the systolic and diastolic pressures have been detected and verified, the augmented value of the pressure sensed at the occurrence of the first K-sound is stored for use as the peak inflation pressure for the next measurement cycle. If, for example, the peak pressure on the first cycle was 160 mmHg, the pressure after the third heartbeat would be 142 mmHg. If the first K-sound were heard shortly thereafter, when the pressure is 140 mmHg, the pressure for the second measurement cycle would be determined to be 160 mmHg. Because the time of occurrence of the K-sound was ideal, the inflation pressure is substantially unchanged. But, if the first K-sound did not occur for a longer time after the third heartbeat, the pressure by that time might be only 120 mmHg, so that the pressure for the second measurement cycle would be reduced to 140 mmHg. Because the initial cycle inflation pressure was too high, a decreased value is used in the succeeding cycle, the reduction being related to the pressure excess as indicated by the delayed occurrence of the K-sound. This feature of the invention minimizes both cuff pressure and the time it is applied, consistent with positive identification of both the systolic and diastolic pressures.

In other embodiments of the invention, the situation where the initial inflation pressure is too high is dealt with in a different manner. In one embodiment, the greatest pressure sensed is incremented for use as the inflation pressure for the next cycle of operation. In another embodiment, the inflation pressure for the succeeding cycle of operation is determined from the greatest pressure sensed in a cycle of operation by increasing it, leaving it the same, or decreasing it, depending on the amount of time that has elapsed after inflation before the first K-sound is heard. This same end result is achieved in the preferred embodiment by recognizing that the longer the first K-sound is delayed the lower will be the pressure when it occurs, resulting in a correction proportional to the pressure excess.

The discrimination circuit reads out, as an output, the systolic and diastolic pressures in parallel form to the digital display and, in serial digital pulse-width-modulated form, in a preferred embodiment. These serial signals from the discrimination circuit are applied to the portable magnetic tape recorder which is part of the system of the present invention.

The recorder is a modified version of that shown in the above-mentioned U.S. Pat. No. Re.29,921. The recorder includes a clock and circuitry for recording an event-marker signal. When the patient experiences coronary symptoms, he activates the event-marker button on the recorder which places an identifiable reference signal on the magnetic tape. The patient is expected then to note the time of the occurrence as shown by the clock of the recorder.

In a preferred embodiment of the present invention, the magnetic tape has two ECG recording tracks. One channel of ECG signals is recorded on the first track, while on the second track, the blood pressure readings, which might normally be programmed at ten or fifteen minute intervals, are multiplexed with another channel of ECG signals and the event-marker signals. Thus, the systolic and diastolic blood pressure readings are recorded on the same trace of the tape as the ECG signal, thereby preserving the time relationship of the signals and facilitating recognition of trends in the data.

The system further includes an electrocardiographic computer and plotter which is a modified version of that shown in the above-mentioned U.S. Pat. No. Re.29,921. The modifications include provision for de-multiplexing the blood pressure readings and the ECG signals which were recorded on the same track. From the ECG signals the computer determines the heart rate. The electrocardiographic computer also includes a plotter for generating a chart on which the heart rate and the blood pressure readings are plotted versus time. In a preferred embodiment, the amplitudes of the heart rate and blood pressure readings are adjusted by the plotter so that a common numerical analog scale can be used to read them. In other embodiments, the systolic and diastolic pressure measurements could be printed on the chart in a digital numeric or alpha numeric means (similar to that described in the aforementioned U.S. Pat. No. Re.29,921) while still maintaining the plot of blood pressure vs. time.

In a preferred embodiment, the B.P.M System is provided with a digital readout which permits the most recently measured systolic and diastolic pressures to be displayed at will.

The present invention provides blood pressure monitoring and recording equipment which is substantially automatic; that is, no patient intervention is required once the cuff has been affixed. However, the pressure measurement cycles may be manually initiated, if so desired.

Further, the present invention provides automated blood pressure monitoring and recording apparatus which is both safe and comfortable to the patient. To this end, a number of safety and comfort features are included which minimize the time during which the cuff is pressurized.

A high degree of accuracy in the blood pressure measurements is obtained by the very novel feature which involves keeping the cuff pressure constant for a measurement period between heartbeats, and by providing for positive identification of the systolic and diastolic pressures with a high degree of artifact rejection through systematic gating.

The present invention facilitates analysis and diagnosis by maintaining a strict time correlation between the signals recorded on the magnetic tape and by providing a patient-activated event-mark, the activation and recording of which correlates to time in a patient diary so that the patient can identify those times during which his symptoms are noticeable.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is a system block diagram of a preferred embodiment of the present invention;

FIG. 3 is a schematic diagram showing portions of the circuit of a preferred embodiment of the B.P.M. System.

FIGS. 6a, 6b, 6c and 6d, is a schematic diagram showing portions of the circuitry of the preferred embodiment of the present invention;

DESCRIPTION OF THE PREFERRED EMBODIMENT

Figure 1:
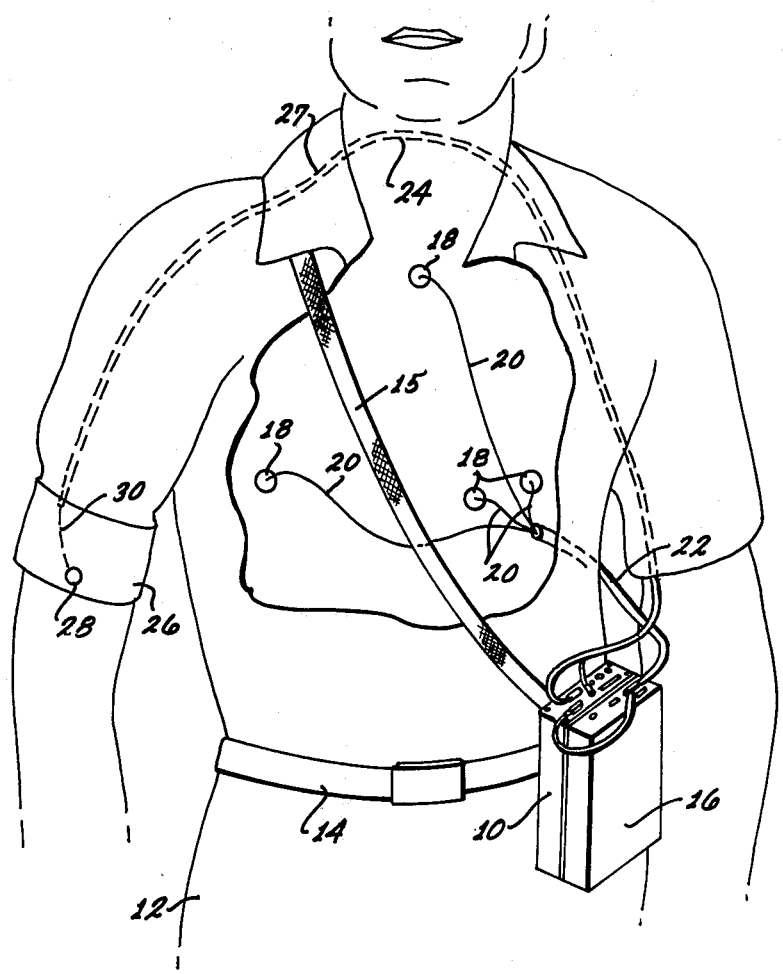
FIG. 1 is a diagram showing the B.P.M. System of the present invention in use.

Turning now to the drawings, in which like parts are identified by the same reference numeral, the use of the B.P.M. System 10 of the present invention is shown in FIG. 1. The B.P.M. System 10 is easily portable and is affixed to the patient 12 by a belt 14 around the patient's waist or by a strap 15, which extends in a loop over a shoulder of the patient 12. A portable tape recorder 16 is also worn by the patient 12, and for convenience the recorder 16 may be affixed to the B.P.M. System 10. A number of ECG electrodes 18 are affixed to the body of the patient 12 in the usual manner in which such electrodes are attached. The lead wires 20 from the ECG electrodes are formed into a cable 22 which is attached to the recorder 16.

A hose 24 extends from the B.P.M. System 10 over the shoulders of the patient 12 to a pressurizable cuff 26 which is affixed to the upper portion of the patient's arm. The hose 24 carries the fluid used for inflating the pressurizable cuff 26 to the cuff. In a preferred embodiment the fluid is air supplied by a pump in the B.P.M. System 10. In other embodiments, a gas could be supplied from a container of compressed gas, or liquid pressure could be employed. A microphone 28 is positioned between the pressurizable cuff 26 and the patient's arm near the distal edge of the cuff 26, as shown in FIG. 1. The microphone 28 converts the Korotkow sounds to electrical signals which are conducted through the microphone cable 30 to the B.P.M. System 10. In a preferred embodiment, the microphone cable is attached to the hose 24 at points along its length.

The B.P.M. System includes a self-contained power supply, consisting of a quantity of battery cells to provide sufficient voltage and capacity to operate the pump, the electronic circuitry and the portable tape recorder continuously for twenty-six hours. In other embodiments, where portability may not be as important, the power could be supplied to the B.P.M. System and recorder by a cable from a fixed source. The portable tape recorder 16 records on a magnetic tape driven continually at a relatively slow speed, so that a single tape is adequate to store twenty-six hours of data. As will be discussed below, in a preferred embodiment, the recorder 16 is capable of recording on two separate tracks of the magnetic tape simultaneously. Whenever sufficient data has been accumulated, the magnetic tape may be removed from the recorder 16 for playback as will be described below.

FIG. 2 is a block diagram of the system for determining, recording, and plotting the patient's heart rate and blood pressure according to a preferred embodiment of the present invention. The system includes the B.P.M. System 10, the portable tape recorder 16 and the modified electrocardiographic computer 32. The pump 34 supplies pressure to the cuff 26 under the control of the valve 36 and the valve control circuit 38. The valve 36, in a preferred embodiment, includes a solenoid-actuated element or core which is spring-biased to a first position when the solenoid is not energized, thereby connecting the cuff to the atmosphere, venting the cuff. When the valve solenoid is energized, the valve element moves to a second position in which the pump 34 is connected to the cuff 26 to pressurize it through the hose 27. In the event power is lost, the valve 36 will be de-energized, thereby venting the cuff 26 and releasing its pressure on the patient's arm.

A separate hose 24 is used to connect the pressure transducer 40 to the cuff 26, permitting the pressure transducer 40 to be packaged within the housing of the B.P.M. System 10, and eliminating the need for power-carrying conductors extending to the pressure cuff 26. The separate hose 24 is connected directly to the cuff 26 rather than to the hose 27 near the valve 36 to avoid sensing the extreme pressure transients that are produced in the hose 27 by the venting action of the valve 36. The pressure transducer 40 generates an electrical signal representative of the cuff pressure which is used for controlling the cuff pressure as well as for measuring the systolic and diastolic blood pressures in the manner described below.

The valve control circuit 38 is responsive to the signal generated by the pressure transducer as well as to a number of other signals described below to control electrically the operation of the valve 36. One of the signals to which the valve control circuit is responsive is a preset pressure determined by the adjustment 42 which generates a signal on the conductor 44 representing a constant preset pressure.

The valve control circuit 38 responds to the preset initial inflation pressure signal on line 44 and to the pressure signal generated by the pressure transducer 40 on the line 46 to selectively energize the valve 36, thereby causing the cuff 26 to be inflated during an initial inflation phase of each cycle of operation. The initial inflation pressure for the first cycle of operation is the value pre-set by the adjustment 42, while in subsequent cycles of operation the peak inflation pressure is determined by the valve control circuit 38 from the systolic pressure measured in the immediately preceding cycle of operation.

Figure 12:
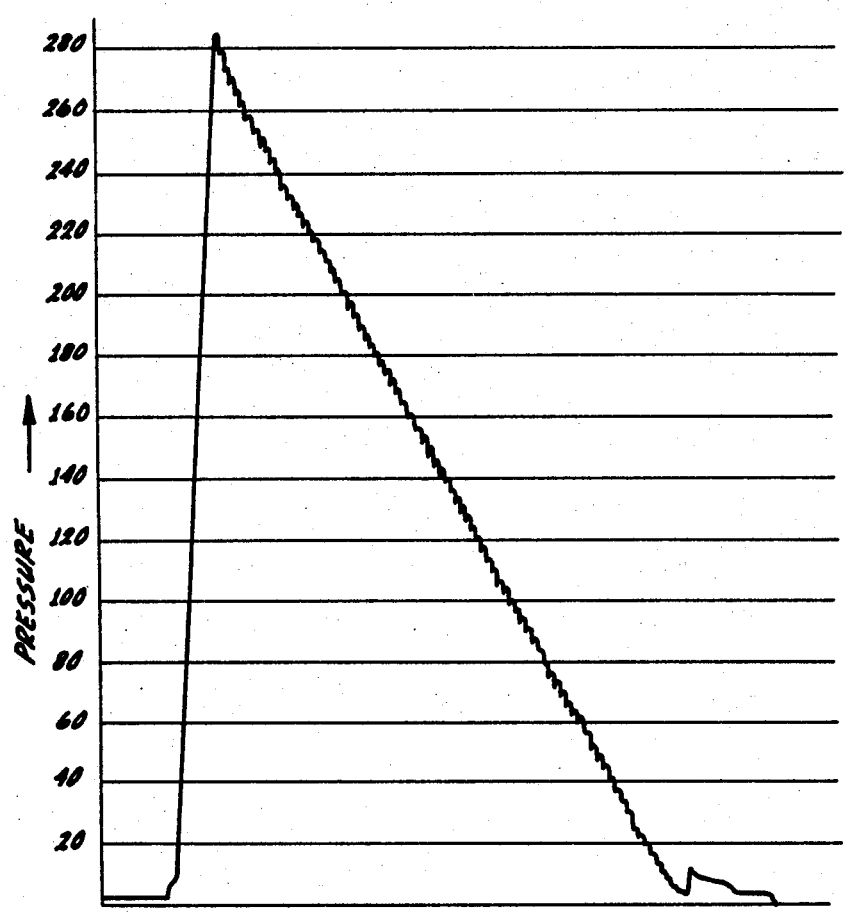
FIG. 12 is a chart showing the cuff pressure versus time within a cycle of operation in a preferred embodiment of the present invention.

After the inflation phase in each cycle of operation, the pressure in the cuff 26 is controlled by the valve control circuit 38 in response to stepping signals developed in the K-sound gate 48 in response to successive R-peaks of the patient's ECG signal, as will be described below. Each of the stepping pulses actuates the valve control circuit 38 to momentarily de-energize the valve 36, thereby letting a small predetermined portion of the fluid pressure in the cuff 26 to be vented to the atmosphere. This results in a substantially linear decrease of cuff pressure with respect to time, as shown in FIG. 12. If the patient's heart is beating at a rapid rate, the pressure decrements will occur more frequently than if the patient's heart is beating slowly.

In prior art systems, employing a linear cuff bleed rate, the rate of pressure reduction was necessarily based on the slowest heart rates anticipated, to prevent too large a pressure decrement between successive measurements, with corresponding decrease in accuracy. As a result, in these prior art systems, the measurement time, determined by the time required for the pressure to decrease from the systolic pressure to the diastolic pressure, was unnecessarily prolonged for patients whose hearts beat faster than the minimum rate anticipated. The present invention overcomes this unnecessary prolongation of the cuff pressure while maintaining the desired accuracy, by pacing the constant reductions of pressure in accordance with the successive heartbeats. Thus, in the present invention, if the patient's heart is beating fast, the measurement cycle will be completed in a shorter time, without sacrifice of accuracy.

The valve control circuit 38 implements the method used in the present invention for venting the cuff immediately after the diastolic pressure has been measured. Again, this is a feature designed to enhance the comfort of the patient by relieving the cuff pressure as quickly as possible. The feature is implemented by a resettable timer in the valve control circuit which operates to de-energize the valve 36 venting the cuff 26 after a predetermined time interval on the order of six seconds or three heartbeats, unless the timer is reset. During the interval between the first K-sound and the last K-sound, resetting signals are applied to the timer by the K-sound gate 48, as will be described below. Upon cessation of the K-sounds, the resetting signals from the K-sound gate 48 terminate, and the timer in the valve control circuit 38 runs down thereby de-energizing the valve 36 and venting the cuff 26 after the diastolic pressure has been determined.

One further aspect of the cuff pressurization system is noteworthy. If, following the initial inflation phase in any cycle of operation, K-sounds are heard within the time required for the first three heartbeats following pressurization, it is an indication that the inflation pressure was less than the patient's systolic pressure. In such an event, determination of the systolic pressure is not possible. Therefore, the discrimination circuit 50 generates a revised inflation pressure which is augmented from the inflation pressure used on the preceding cycle by a predetermined amount and also generates a signal to activate the pump 34 so that further inflation of the cuff will result immediately. This feature is particularly valuable in the automatic blood pressure measuring system of the present invention to prevent a false identification of the systolic pressure.

Continuing with the description of the system block diagram of FIG. 2, the clock 52 provides repetitive signals at fifteen-minute intervals for use in initiating successive measurement cycle. The clock 52 also provides clock pulses on separate lines at 8192 Hz for the A-to-D converter 54, 1024 Hz for the K-sound gate 48, 32 Hz for the data encoder 56 and pressure memory 58, in a preferred embodiment. The detailed operation of these various circuits will be described below.

Aside from the cuff pressure control and system timing functions, most of the decison-making functions of the B.P.M. System are implemented in the discrimination circuit 50. As mentioned above, the essential data inputs to the discrimination circuit 50 are the ECG signal on line 60, the K-sound signal on line 30 and the pressure data signal on line 46. From these signals, the discrimination circuit 50 determines the systolic and diastolic blood pressure of the patient, the blood pressure data being presented on line 62 for recording on the portable tape recorder 16.

In a preferred embodiment, the signals sent by the ECG electrodes 18 are carried by the cable 22 to the portable tape recorder 16 to be recorded. Although several channels of ECG information could be obtained and recorded, in the preferred embodiment two channels are used. One of those channels is transferred on line 60 to the discrimination circuit for use in determining the time of occurrence of the successive R-peaks. In the preferred embodiment, the K-sound transducer 28 is a microphone which converts the accoustical K-sounds to an electrical signal, which is presented on the microphone cable 30. In the preferred embodiment, the output of the pressure transducer 40, on the line 46 is an analog signal which is converted to digital form by the analog-to-digital converter 54. In other embodiments, a pressure transducer having a digital output may be used.

As described above, in the auscultatory method of sensing blood pressure, a trained person listens for and identifies the K-sounds. In the present invention, this sophisticated identification is implemented by the discrimination circuit 50 as will now be briefly described. A much expanded discussion will be given below in connection with the schematic diagrams of FIGS. 3-6 and the logical flow chart of FIG. 11.

The ECG signal on the line 60 of FIG. 2 is applied to the R-filter 64, which suppresses the higher and lower frequencies present in the signal and which uses the leading edge of the R-peak to generate an R-pulse of predetermined width on the line 66. These recurring R-pulses are taken as marking the times of occurrence of successive heartbeats. Similarly, the K-sound signal on the microphone cable 30 is filtered by the K-filter 68, which removes the higher and lower frequency components of the signal, and which generates therefrom a succession of K-pulses of predetermined pulse width on the line 70, which mark the times of occurrence of successive K-sounds. By suppressing the other frequency components, the K-filter 68 tends to reject artifact noises, which are known to be of higher frequency generally than the K-pulses.

Figure 14:
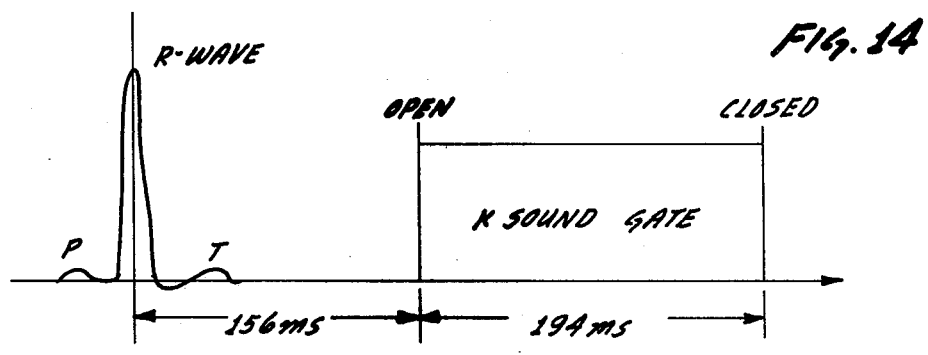
FIG. 14 is a chart showing the relation between the K-sound gate and the ECG signal in a preferred embodiment of the present invention.

After the initial inflation phase of each cycle of operation, each successive R-pulse on the line 66 establishes an initial time used by the K-sound gate 48 to establish a time interval, following arrival of the R-pulse, during which the K-pulse on line 70 should occur if it is going to. The preferred embodiment of the present invention implements the fact that the K-sound normally occurs no sooner than 156 milliseconds after the R-peak and no later than 350 milliseconds after the R-peak. Consequently, if a K-sound is to be regarded as valid it must occur within a 200-millisecond interval that begins 156 milliseconds after the R-pulse. The K-sound gate is illustrated in FIG. 14.

If a K-sound is detected during the interval, a gated K-pulse will be generated, and if no K-sound is detected during the time interval, a $\overline{K}$-pulse will be generated by the K-sound gate 48.

The $\overline{K}$ and gated K-pulses are applied to the artifact rejector 72 in which the identification function is implemented. The first time a gated K-pulse occurs, the digitalized present value of the pressure is entered into the pressure memory 58 from the analog to digital converter 54 as a systolic measurement. After the K-sound gate has closed the cuff pressure is dropped three millimeters of mercury, and then another R-pulse occurs. The artifact rejector 72 requires that another K-sound, following the second R-pulse must occur if the onset of gated K-pulses is to be regarded as valid and not caused by artifact noise. If the second K-sound does not occur, the conclusion is that the first K-sound was artifact noise. In this case, the pressure data fed into the pressure memory 58 is discarded and the system awaits the next R-pulse. If the second gated K-pulse occurs following the second R-pulse, the stored systolic pressure is preserved and the now-current pressure is read into the pressure memory 58 as a potential diastolic pressure. Successive pressure values are read into the pressure memory 58 so that its contents are repeatedly updated. The final pressure value remaining in the pressure memory 58 at the time the diastolic pressure is identified becomes the measured diastolic pressure.

In a preferred embodiment of the present invention, the artifact rejector 72 is responsive to the generation following successive heartbeats of three $\overline{K}$-signals followed by two K-signals to identify the pressure associated with the first gated K-signal as being the systolic pressure. Similarly, the artifact rejector 72 responds to the generation, following successive heartbeats of two gated K-signals followed by three $\overline{K}$-signals to identify the pressure associated with the last gated K-signal as the diastolic pressure.

Following acquisition of the diastolic pressure, the artifact rejector 72 actuates the pressure memory 58 to produce a serial readout of the systolic and diastolic pressures and actuates the data encoder 56 to convert the serial digital output of the pressure memory to a serial FM data stream on line 62.

The portable tape recorder 16 is similar to that described in U.S. Pat. No. Re.29,921 filed for "Electrocardiographic Computer", by I. Raymond Cherry and Donald L. Anderson. In the recorder described therein, the person carrying the recorder can manually superimpose an event marker signal onto the ECG signal recorded on one of the tracks of the tape. In the present invention, the tape recorder of the foregoing patent has been modified so that the presence of serial digital pulse-width modulated data (hereafter abbreviated DPWM) on the line 62 will be given priority for recording over the event marker signal which, in turn, had priority over the ECG signal. This control priority scheme assures that no blood pressure data will be lost. Because only three-quarters of a second is required to read in the serial DPWM data, a simultaneously-occurring event marker signal would still be recognizable (though interrupted) because of its longer duration (approximately one second in a preferred embodiment).

Figure 7:
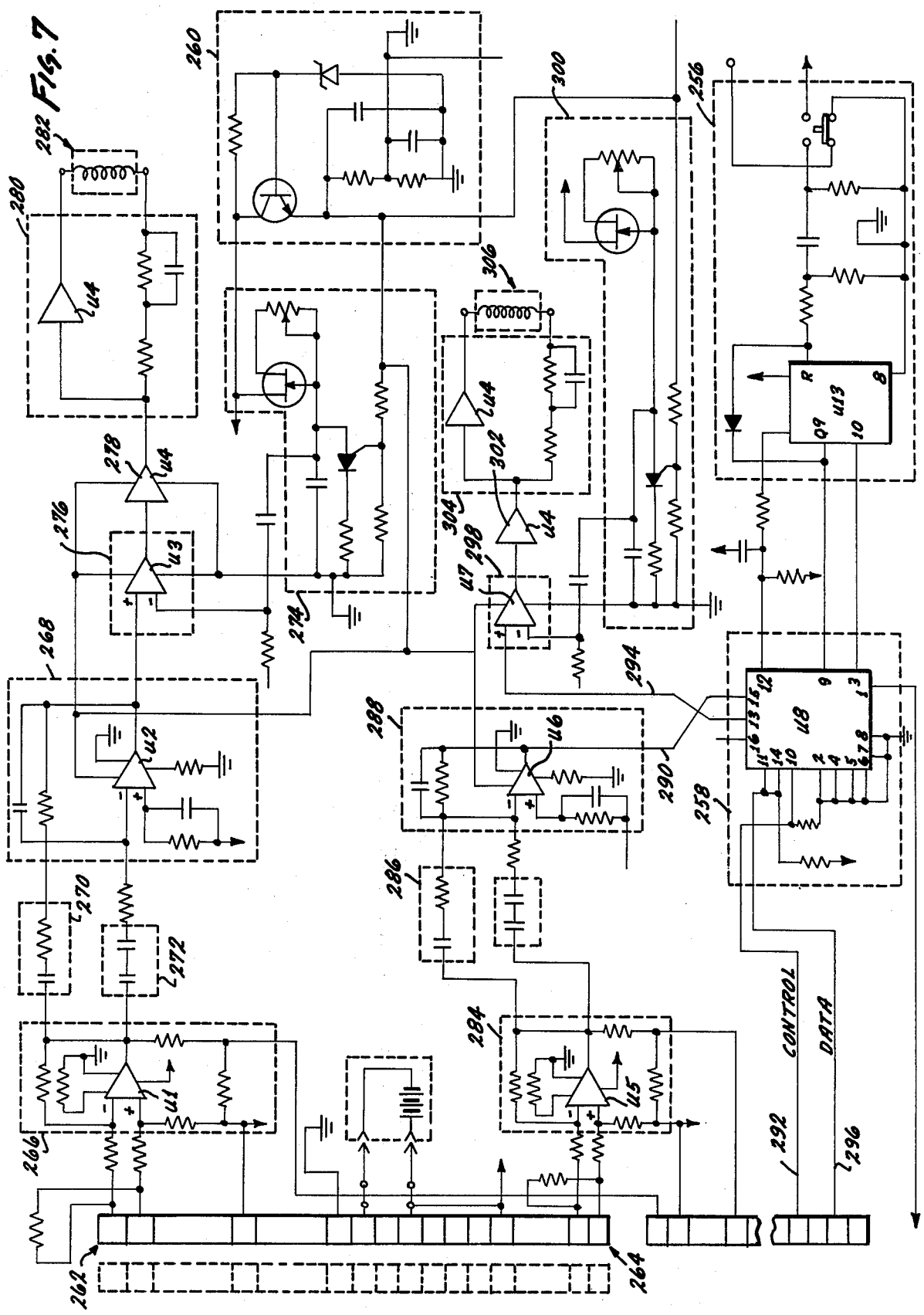
FIG. 7 is a schematic diagram of the circuitry of a tape recorder for use with the B.P.M. System of the present invention.

In a preferred embodiment, the portable tape recorder 16 has provision for simultaneously recording on two tracks of the magnetic tape 74. One of the tracks, 73, is dedicated to a channel of ECG signals while on the other track, 75, the blood pressure data, event marker, and a second channel of ECG signals are selectively recorded. In a preferred embodiment of the present invention, the magnetic tape 74 is of sufficient length that up to twenty-six hours of consecutive data can be recorded on it at the recording speeds used (0.0625 inches per second in a preferred embodiment). It is, of course, not necessary to record for the entire twenty-six hour duration of the tape, and the magnetic tape 74 provides a compact and convenient means of storing whatever data is recorded on it. Subsequent playback of the tape on the electrocardiographic computer 32, as described below, does not destroy the information recorded on the tape. A schematic diagram of the circuitry of the portable tape recorder 16 is shown in FIG. 7.

Figure 10:
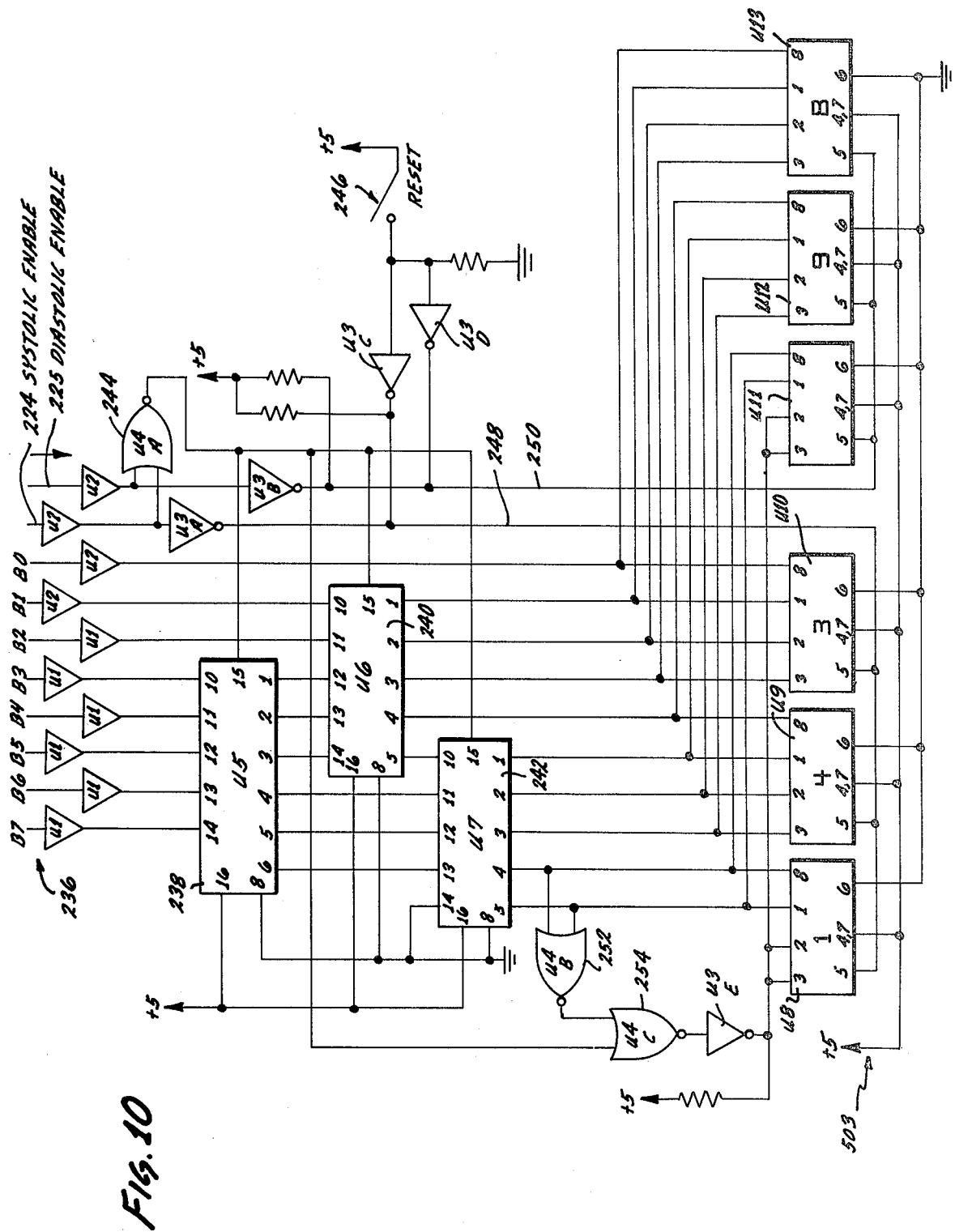
FIG. 10 is a schematic diagram showing the circuitry of a digital read-out for use with the B.P.M. System of the present invention.

In one embodiment of the present invention, the B.P.M. System is provided with a digital display circuit 76 to permit the measured systolic and diastolic blood pressures to be displayed by LED displays or liquid crystal readouts in the form of two 3-digit decimal numbers, which are displayed until cleared by a reset switch or until a new measurement has been completed. The digital display feature permits the current readings to be obtained without interrupting the recording process. A schematic circuit diagram of the digital display circuit is shown in FIG. 10.

In accordance with a preferred embodiment of the present invention, the magnetic tape 74 is removed from the portable tape recorder 16 and inserted into the electrocardiographic computer 32 for analysis and plotting. The electrocardiographic computer 32 is similar to that disclosed in U.S. Pat. No. Re. 29,921 by Cherry and Anderson. As disclosed therein, the electrocardiographic computer included a tape playback unit 78 for converting the recorded signals to electrical form, a heart rate trend computer 80 responsive to the ECG signal to produce a heart rate signal indicative of the rate at which the patient's heart was beating, and also included a plotter 82 for producing a chart 84 of the heart rate versus time.

According to a preferred embodiment of the present invention, the electrocardiographic computer 32 is modified by the addition of a data decoder 86 which recognizes and separates the blood pressure data from the ECG data and which produces a control signal when the blood pressure data is present. The electrocardiographic computer 32 of the prior reissued patent has been further modified by the addition of a multiplexer gate 88 responsive to the control signal produced by the data decoder 86 to selectively pass the heart rate signal or the blood pressure signal when it is present. The electrocardiograhic computer 32, as disclosed in the above-identified reissued patent included provision for indicating on the chart 84 the points at which the event marker was activated.

Figure 8:
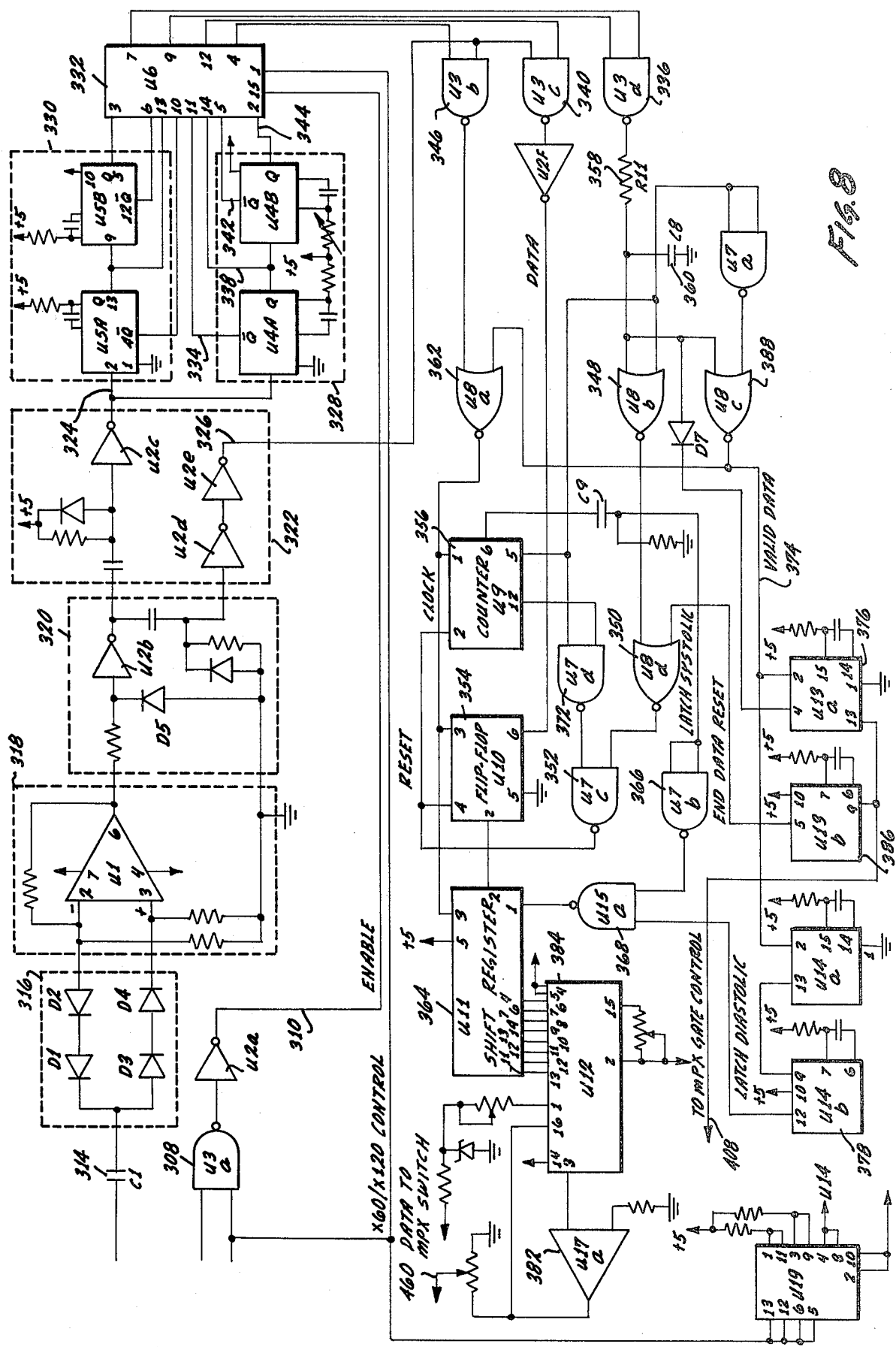
FIG. 8 is a schematic diagram showing a preferred embodiment of the data decoder used with the B.P.M. System of the present invention.
Figure 9:
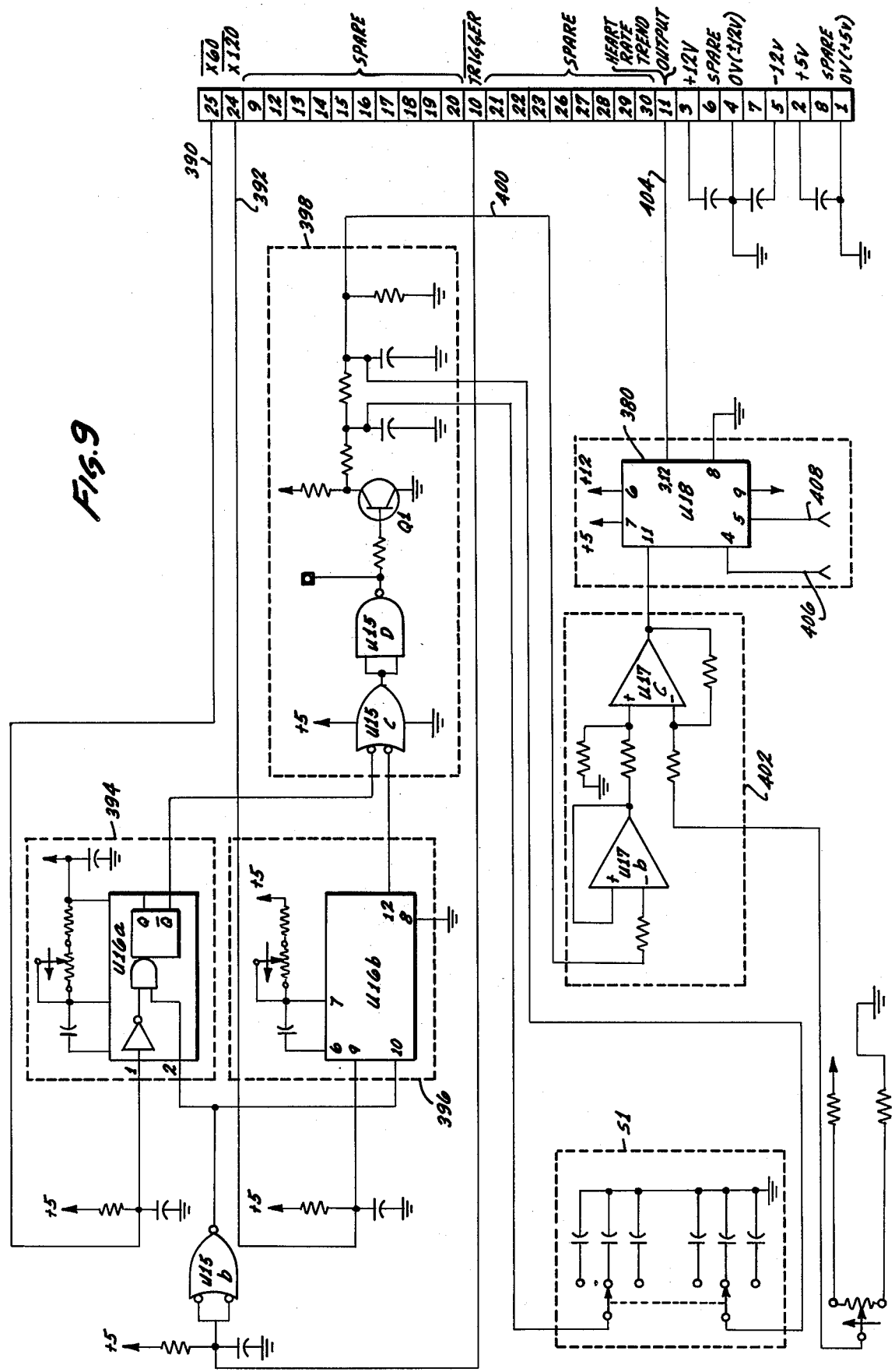
FIG. 9 is a schematic diagram showing a preferred embodiment of a heart rate trend computer used with the B.P.M. System of the present invention.

Schematic circuit diagrams of the data decoder 86 and the heart rate trend computer 80 are shown as FIGS. 8 and 9 respectively. The multiplex gate 88 is indicated by reference numeral 380 of FIG. 9.

In summary, the system shown in FIGS. 1 and 2 embodies a method of producing an improved presentation of heart-related data to facilitate the diagnosis of heart disorders, by sensing continually an ECG signal produced by the patient, measuring the patient's blood pressure at intervals by the use of portable apparatus affixed to the patient, and recording both the ECG signal and the blood pressure signal on a single track of a magnetic tape. The magnetic tape is later played back at a faster rate than that at which it was recorded to produce a combined electrical signal representing both the ECG signal and the blood pressure signal. These latter two signals are then separated by a data decoder and a heart rate signal is produced from the ECG signal. Finally, both the blood pressure signal and the heart rate signal are plotted versus time on the same chart to facilitate diagnosis.

The remainder of the description will be devoted to a further elaboration of those portions of the B.P.M. System which might not be regarded as straightforward extensions of the prior art. The power supply, system timing, discriminator circuit 50 and valve control circuit 38 will be described in connection with FIGS. 3-6, which show these circuits in schematic form.

In a preferred embodiment, power for the B.P.M. System is supplied by several nickel cadmium cells connected to form a 7.5-volt battery. The motor driving the pump 34 and the solenoid for actuating the valve 36 are driven through transistor switches from this supply. For use in the electronic circuitry of the B.P.M. System, a regulated voltage of five volts is developed by the regulator U24, 90 of FIG. 3, and the resistors R11 and R12. The transistor Q3 is an emitter follower to provide more current than U24 alone can supply.

Figure 5:
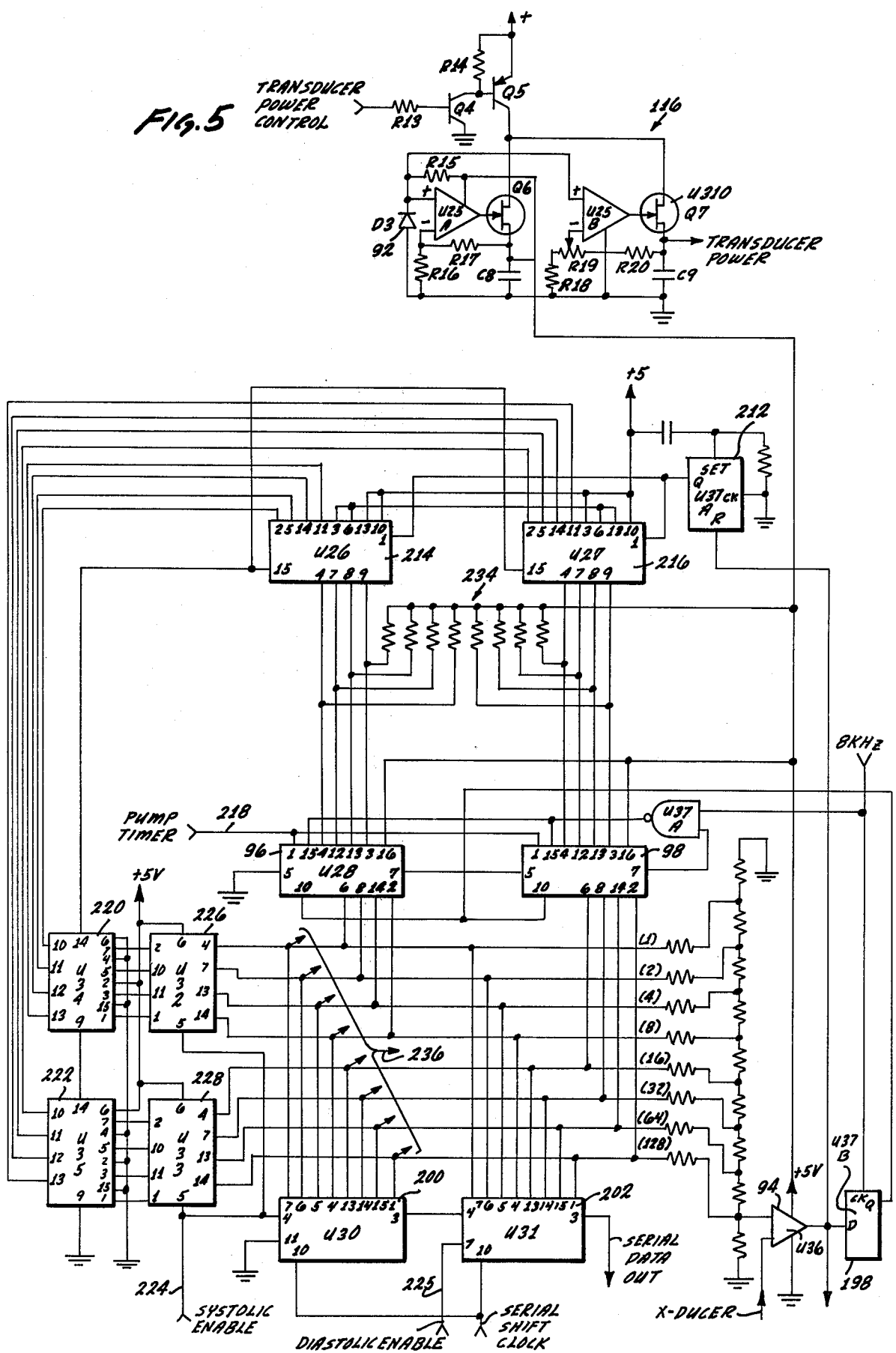
FIG. 5 is a schematic showing portions of the circuitry of the preferred embodiment of the present invention.
Figure 6:
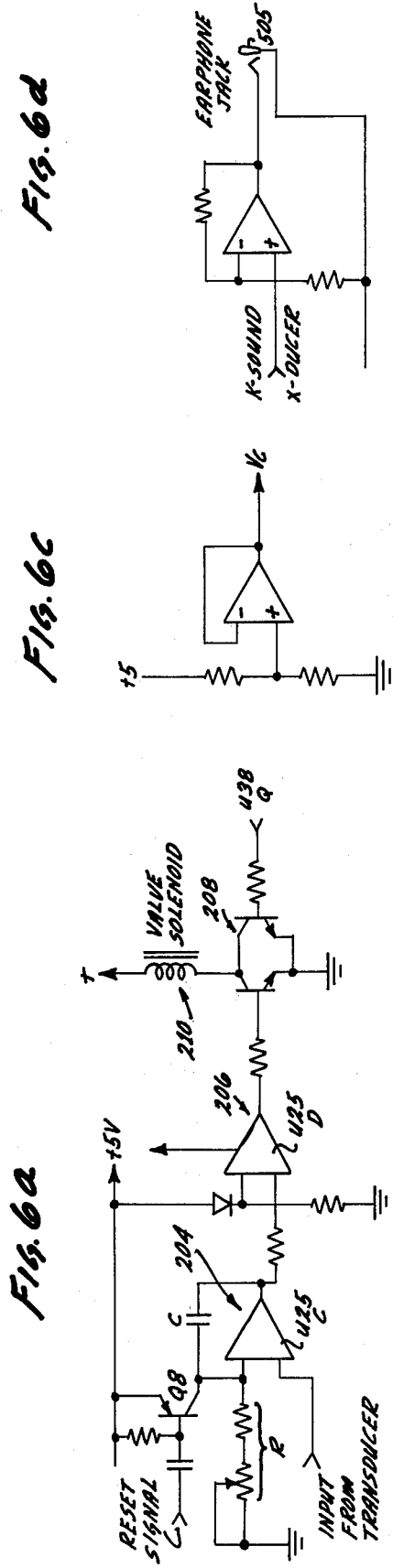
FIG. 6, including

Two separate switched power supplies are provided to supply current to the pressure transducer 40 and the comparator U36 portion of the valve control circuit, as shown in FIG. 5. These supplies are switched on and off to reduce power consumption between measurement cycles. Transistors Q4 and Q5 provide the level shift and switching functions. When these supplies are switched on, the reference diode D3, 92 of FIG. 5, provides a stable temperature-compensated 1.220 volts to reference both supplies. U25a and resistors R16 and R17 provide a fixed 5-volt supply. The transistor Q6 is used as a current booster. This supplies the comparator 94 of FIG. 5 and the analog to digital converter counters U28 and U29, 96 and 98 of FIG. 5, respectively. The supply generated by U25B and transistor Q7 for the transducer is adjustable to compensate for differences in transducers and variations in the five volts received from U25A.

All system timing is generated from a crystal-controlled oscillator, 100 of FIG. 3, formed by U22A and U22B, resistors R1 and R2, capacitor C1 and crystal X1. The output of this circuit on line 102 is a square wave having a frequency of 16,384 Hz. The counter U1 divides the basic oscillator frequency to provide signals having several other frequencies including: 8192 Hz (8 KHz) clock pulses for the analog to digital converter, 1024 Hz for the K-sound gating circuits, 32 Hz for output data encoding, and a one-second clock signal. The counter U2 divides the one-second clock signal produced by the counter U1 for other system use. The output of the counter as sensed by U4 provides a basic fifteen-minute interval. U6A and U5B decode the 128-second count following cycle initiation to shut down if a measurement cycle exceeds this period of time. The 16-second output is utilized as a pump shut-off safety. Taken together, the counters and gates constitute the timing signal generator 104 of FIG. 3.

During the interval between measurement cycles, both of the flip-flops U3A and U3B 106 and 108 of FIG. 3, respectively, have Q outputs at logic zero, and $\overline{Q}$ outputs at logic 1. The JK inputs of U3A are tied to logic 1 and the flip-flop will change state on a positive clock transition. The J input of U3B is tied to U3A's $\overline{Q}$ output and is at logic 1, U3B's K output is at logic zero (U3B's Q output) and the flip-flop will change state on a positive clock transition.

When the 512-, 256-, and 128-second outputs of the counter U2 all reach logic 1, the output of NAND gate U4A goes to logic zero and gate U5A goes to logic 1, clocking the flip-flops U3A and U3B. The logic 1 level also resets the counter U2 via line 110, and thereby returning U5A's output to logic zero. The Q outputs of both U3A and U3B are now at logic 1, which switches on the pump via line 112, closes the valve via line 114, and switches on the power supply 116 of FIG. 5 for the comparator 94 of FIG. 5, and for the pressure transducer.

The counter U2 provides an output on line 118 after 16 seconds have elapsed, the output going high to reset the flip-flop U3B, 108, through the OR gate U13A 120. The pump also will be turned off by a signal from the comparator 94 of FIG. 5 applied to the OR gate 120 of FIG. 3.

After 128 seconds from the start of a measurement cycle, the NAND gate U5B, 122, decodes the 128-second condition, and the logic zero signal from U5B drives the output of the AND gate U11C, 196, low, resetting all the decision logic including the flip-flop U3A, ending the measurement cycle. A new cycle will be initiated in 12.8 minutes.

A new measurement cycle may be started or the current one may be stopped at any time by use of the start/stop switch S1, 126 of FIG. 3. The NOR gate U15A is used as an inverter and its output is logic zero when the switch S1 is open. The input of the inverter U6E, 128, is grounded through the resistor R10 so that the output of U6E is high. When the switch S1 is closed, the output of U15A switches to a logic 1 state. The switching transient charges the capacitor C through the internal diodes of the inverter U6E, causing the input of U6E to rise briefly to +5 volts before discharging through R10 to ground. After approximately one microsecond, the input to U6E reaches a logic zero level. The output of U6E is a one-microsecond negative pulse which resets the counters U1 and U2 and which clocks the flip-flops U3A, 106, and U3B, 108, through the NAND gate U5A, starting a measurement cycle. If a cycle had been in progress when the switch S1 was depressed, the K input of U3B would have been logic 1, and U3B will reset through the clock. U3A will always change state with the clock and will also reset.

If the initial inflation phase of the measurement cycle is complete and the measurement phase is under way, both the J and K inputs of U3B are logic zero, and it will not change state with the clock. When the measurement has been completed and the system is waiting to begin the next cycle, various counters and registers are in an unknown condition, but after 128 seconds, a logic zero output of U5B, 122, will drive the reset line 130 to logic zero, resetting all circuitry.

Figure 4:
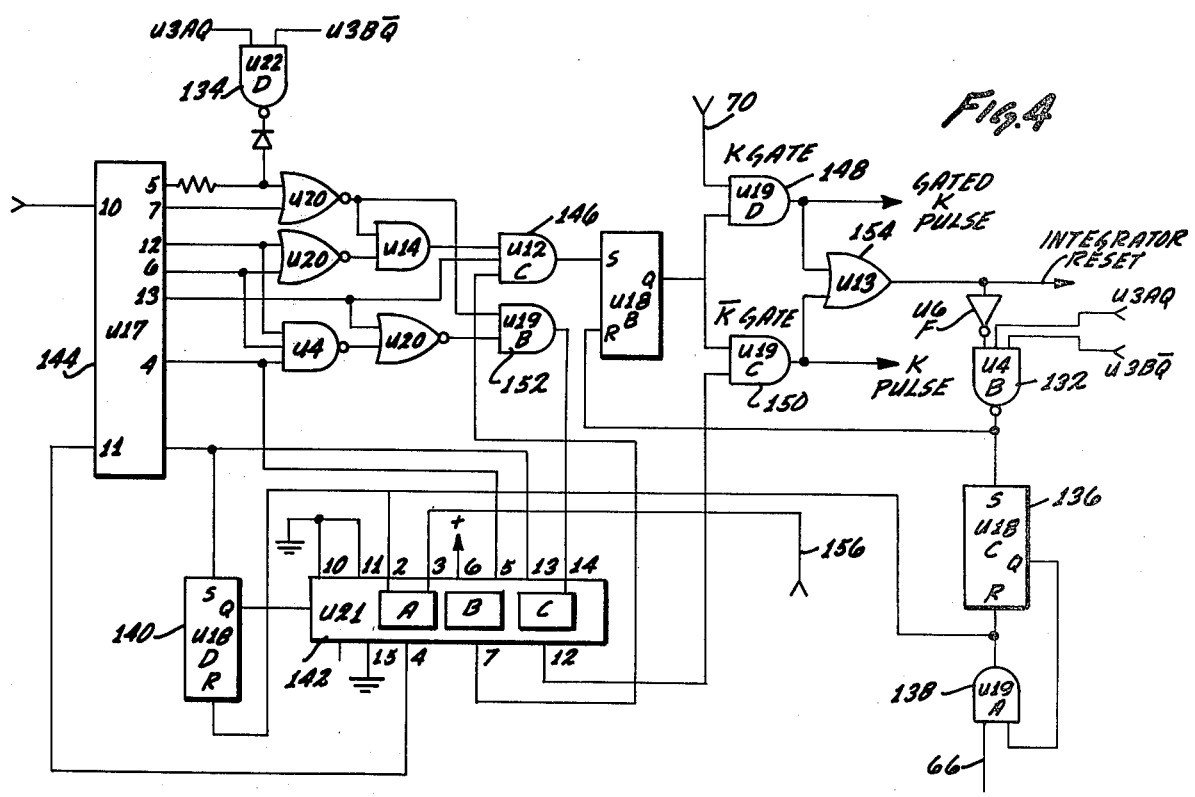
FIG. 4 is a schematic diagram showing certain portions of the circuitry of the preferred embodiment of the B.P.M. System.

Referring now to the schematic of the K-sound gate shown in FIG. 4, the generation of K and $\overline{K}$ pulses is disabled by NAND gates, U4B, 132, and U22D, 134. When pressurization has been completed, output K and $\overline{K}$ pulses are enabled.

When the flip-flop U18C is in the set condition (Q output=logic 1) an R-wave pulse from the R-filter 64 enters the AND gate U19A and resets the flip-flop U18C, disabling further R-wave inputs. The output of U19A is a narrow pulse, approximately one microsecond in width, which resets the flip-flop U18D, 140, of FIG. 4, passes through the multiplexer U21, 142, from pin 2 to pin 4, to reset the counter U17, 144. Thereafter, the counter U17 now counts at a 1024 Hz rate and the 156 millisecond count condition is detected at the output of the AND gate U12C, 146. This sets the flip-flop U18B, which in turn enables both the K and $\overline{K}$ AND gates U19D, 148, and U19C, 150. As described above, these gates are than held open during the succeeding 200 milliseconds, until the 350 millisecond count condition is detected at the output of the AND gate U19B, 152, which causes a logic 1·signal to pass through the multiplexer U21, 142, from pin 14 to pin 12 to provide a positive-going transition at the $\overline{K}$-gate, U19C, 150, to produce the $\overline{K}$-pulse. The logic 1 level also propagates through the OR gate U13, 154, setting the flip-flop U18C, 136, and resetting the flip-flop U18B ending the gating period. The width of the output pulses from the $\overline{K}$ gate 150 and the OR gate 154 is approximately 1.2 microseconds. The K-sound gate must now await another R-wave to initiate the generation of the next K-gate interval. FIG. 14 shows the K-sound gate.

If a K-sound is detected during the gate interval, a gated K-pulse is produced by the K-gate U19D, 148, which pulse also resets the flip-flops U18C, 136, and U18D, 140, inhibiting the $\overline{K}$-pulse.

If the R-waves are interrupted for more than two seconds, the flip-flop U18D, 140 is set, placing the system into a different, ungated, mode of operation. In that mode, the system generates internally a substitute for the absent R-waves in the form of a sequence of two-second time intervals which are analogous to the intervals between successive heartbeats. It is noteworthy that the present invention can provide systolic and diastolic blood pressure measurements even if the ECG electrodes are not attached to the patient.

In response to the setting of the flip-flop U18D, 140, the multiplexer U21, 142, switches from inputs 2, 5 and 14 to inputs 3, 6 and 13. This permits the logic 1 level which has set the flip-flop U18D to now pass through the multiplexer U21, from pin 13 to pin 12 to form a $\overline{K}$-pulse through the $\overline{K}$-gate u19C, 150 and also generating a reset pulse through the OR gate U13, 154. The effect of the reset pulse from U13 is to de-energize the valve 36 for pressure release, and while the valve is de-energized, a signal on the line 156 is propagated through the multiplexer 142 to reset the counter U17, 144. At the end of the period of de-energization, the counter U17 begins to count, and after 95 milliseconds, U18B is set opening the K-gate. The 95 millisecond delay is necessary for cuff noise to dissipate following re-energization of the valve 36. The K-gate now remains open until either a K-sound occurs or until two seconds elapse which will result in a $\overline{K}$ signal. Either condition steps down the pressure in the cuff 26 and restarts the de-energization timer of the valve control circuit. If an R-wave is detected, the flip-flop U18D, 140, is reset and the gating action returns to normal.

As shown in the block diagram of FIG. 2, the inputs to the K-sound gate 48 are the signals on lines 66 and 70 from the R-filter 64 and the K-filter 68, respectively. The circuits of these filters are very similar, differing only in the time constant used in the filter. Therefore, the filter circuit shown in FIG. 6b can be employed in both the K-filter and R-filter. As shown in FIG. 6b, the filter includes an isolation stage 158, a low-pass amplifier 160 whose gain is down 3 db at 120 Hz, a filter stage 162 followed by a high-pass amplifier 164 whose response is down 3 db at 40 Hz. The output of the high-pass amplifier is connected to the comparator 166 which acts as a threshold to pass only those parts of the signal which are more negative than some preset threshold level, namely the R peaks of the ECG signal. The NAND gate 168 is used as an inverter to cause the K or R pulses to have a positive polarity. FIG. 6c shows the voltage divider arrangement used to provide a local ground for the filter circuit.

Returning now to the description of the schematic of the discriminator circuit 50 as shown in FIG. 3, when the power is first applied, the flip-flops U8A, 170 and U8B, 172, are reset ($\overline{Q}$-output is high). The $\overline{Q}$-output of the flip-flop U8A holds the counter U7, 174, in the reset condition through OR gate U13B. After the pump motor has been turned off, $\overline{K}$ and gated-K pulses will issue from the K-sound gate as previously described.

The $\overline{Q}$-output of U8B, 172, is connected to its J and K inputs. When $\overline{Q}$ is high, the flip-flop U8B will dchange state on a negative-going pulse. The $\overline{Q}$-output of U8B is also connected to the K-input of the flip-flop U8A, andthe Q-output of U8B is connected to the J-input of the flip-flop U8A. Following reset, U8A will have its $\overline{Q}$-output high and clock pulses force the same condition. U8B will have $\overline{Q}$ high and Q low, but will change state with a negative-going pulse.

The AND gate U11B is enabled by U8B's $\overline{Q}$-output and controls the systolic storage register. The Q-output of U8B controls the AND gate U11A and the diastolic storage register. Following reset, U11B is enabled and U11A is disabled.

Cuff pressure will normally be above the systolic blood pressure and no K-sounds will occur initially. K-pulses will not be counted by the counter U7, 174, because that counter is held in the reset condition by the $\overline{Q}$-output of the flip-flop U8A initially, as described above. $\overline{K}$-pulses will also pass through the AND gates U14A and U14B to reset the flip-flop U8B, 172, which initially is already in the reset condition.

As the cuff pressure drops, the systolic pressure is reached and a K-sound is detected. The positive edge of this K-pulse as it passes through the AND gate U11B clocks the present state of the analog-to-digital converter 54 of FIG. 2, into the systolic register portion of the pressure memory 58 of FIG. 2. The falling edge of the pulse then clocks the flip-flop U8B. Its $\overline{Q}$ output now goes low, disabling the systolic register input, so that the value read in will not change. The Q-output of the flip-flop U8B goes to its high state enabling the diastolic gate U11A. The U8B $\overline{Q}$-output is fed back to its J and K inputs, holding both of them low so that further K-pulses wil not change its state.

The J and K inputs of the flip-flop U8A have now changed state with J high and K low. Assuming each heartbeat is now followed by a K-sound, the second K-pulse will enter the then-present pressure value produced by the analog-to-digital converter 54 of FIG. 2 into the diastolic register on occurrence of the positive edge of the K-pulse and will clock U8A so that its $\overline{Q}$-output is the same as the K-input (both low). A low level on $\overline{Q}$ releases the reset condition of the counter U7 so it can count and disables the AND gate U14A so that the flip-flop U8B, 172, cannot be reset. Subsequent K-pulses now clock new data into the diastolic register and have no effect on other circuits.

When the cuff pressure has dropped below the diastolic pressure, the K-sounds cease. A $\overline{K}$-pulse now follows each heart beat, and these $\overline{K}$-pulses are counted by the counter U7, 174. When three consecutive $\overline{K}$-pulses have been counted, the "3" output goes high and disables further counting. The inverter U6C inverts the signal from the counter U7 and disables the AND gates U11A and U11B, preventing further data to be entered into the pressure memory 58 from the analog-to-digital converter 54 of FIG. 2.

Until this time, the inverter U6C has held the counter U9, 176, in the reset condition, and the multiplex control line 178 in the "data off" state through the NOR gate U15D, 180. The flip-flop U10A, 182, has also been held in the reset condition, with Q-output low.

When the output of the inverter U6C goes negative, the data output circuitry is enabled and the multiplex control line 178 goes high. The data output switch U16, 184, is still in the "off" state. The counter U9 is now enabled to count the 32 Hz input clock signal. After four clock periods, pin 6 of the counter U9, 176, goes high and the flip-flop U10A, 182, changes state, allowing clock pulses to pass through the AND gate U14C, 186, to turn on the data output switch U16, 184.

Clock pulses are now converted to positive-going pulses at the input of the NAND gate U5C, 188, and to negative-going pulses at the input of the NAND gate U5D, 190. The pulses appearing at the input of U5C are passed to its output only when its other input is positive, corresponding to a "1" bit in the pressure storage registers. Pulses at the input of U5D shift the data held in the storage registers one place to the right, and always change the state of the flip-flop U10B, 192. Pulses passed by U5C also pass U5D to change the output state of the flip-flop U10B, 192. Thus, the pressure data stored in digital form in the pressure memory 58 is converted to an FM data stream by the circuit, which is the data encoder 56 of FIG. 2.

After sixteen more clock pulses (a total of 20), all the data in the pressure memory has been shifted out of the registers. The flip-flop U10A, 182, is then reset and the data output switch 184 is turned off. The multiplex control line 178 is held high for four more clock pulses. The output of the NOR gate U15D, 180, then goes to logic 0.

The negative transition at the output of the NOR gate 180 is formed into a negative-going pulse by the capacitor C3, 194, for application to the AND gate U11C, 196. The negative pulse out of AND gate U11C resets the control flip-flops U8A, 170, and U8B, 172, and the cycle control flip-flops U3A, 106, and U3B, 108, ending the measurement cycle.

The rejection of falsely high systolic measurements caused by artifact noises is provided by the flip-flops, U8A, 170, and U8B, 172. The first K-sound enters systolic data and enables the diastolic register. If a K-sound is not detected following the next heart beat (R-pulse), a $\overline{K}$-pulse must occur. This $\overline{K}$-bar pulse will be passed by the AND gates U14A and U14B to reset the flip-flop U8B, 172, allowing a new systolic pressure measurement. The diastolic measurement must be followed by the consecutive absence of three K-sounds. To ensure this, the $\overline{K}$-counter, U7, 174, is reset by each K-pulse.

The schematic diagram of FIG. 5 shows the analog-to-digital converter and storage registers used in a preferred embodiment of the present invention. The counters U28, 96, of FIG. 5 and U29, 98, are "4"-bit binary counters connected in series to provide a single "8"-bit counter. This counter can count up or down. The direction of count is controlled by the flip-flop U37B, 198, and the comparator U36, 94, of FIG. 5.

The outputs of the counters 96, 98 are connected to the two "8"-bit storage registers U30, 200, and U31, 202, and to an R-2R ladder network. The ladder network converts the "8"-bit number from the counters to a DC voltage level. This level and the pressure transducer output are presented to the comparator U36, 94, for comparison.

If the ladder voltage exceeds the transducer voltage, the output of the comparator U36 is low. On the next negative clock pulse edge, the Q-output of the flip-flop U37B, 198, will be low, setting the counters in the downward-counting mode. On the next positive clock pulse edge, the counter will count down one count, reducing the voltage level at the comparator. If the ladder output is still above the transducer output, counting down will continue with each positive-going clock pulse edge.

If the ladder output is less than the transducer output, the output of the comparator U36, 94, goes high. On the following negative clock edge, the Q-output of the flip-flop U37B, 198, goes high, putting the counter in the upward-counting state. Now the counter will be incremented on each positive clock pulse until the ladder output again exceeds the transducer input.

Usually, the level of the output of the transducer will be between two discrete ladder steps, and the output of the counters 96-98 will alternate (dither) above and below the transducer output level.

If the transducer level is beyond the input range of the analog-to-digital converter, a "carry-out" signal will be produced at pin 7 of the counter U29, 98. This signal disables the operation of the counters until the transducer output level is again within the input range of the analog-to-digital converter.

After cuff inflation has been completed in each cycle of operation, pressure release during the measurement phase is controlled by a constant difference pressure step circuit, shown in FIG. 6a. This circuit consists of an integrator 204 and a comparator 206. Pulses from the OR gate U13, 154, of FIG. 4, trigger the dump transistor Q8, 208, discharging the integrator capacitor C and causing the output of U25C to go to ground. This in turn will cause the output of the comparator U25D to be low so that the power to the valve solenoid 210 is cut off. The valve, being deenergized, now vents some of the air in the cuff to the atmosphere. After the reset pulse has expired, the integrator 204 begins to integrate towards the positive supply voltage. When the output of the integrator 204 reaches approximately 4.3 volts, the comparator U25D changes state closing the valve again.

The rate of integration is approximately equal to 4.3 RC/E, where C is the capacitance of the capacitor C, R is the resistance shown in FIG. 6a, and E is the input voltage to the integrator from the pressure transducer. By proper choice of the RC time constant, the pressure difference between successive steps can be adjusted to any chosen value. In a preferred embodiment, the pressure step is set at 3 mmHg. For a constant heart rate, the cuff pressure has the form of a decreasing linear staircase as shown in FIG. 12.

Referring now to the schematic diagram of FIG. 5, the circuitry for controlling the cuff pressure will be described. At the beginning of the first measurement cycle, when power is first applied, the flip-flop U37A, 212 of FIG. 5, is set by the resistor and capacitor that are connected to its set input. This places a preselected fixed binary number with the decimal value of 180 at the outputs of the multiplex gates U26, 214, and U27, 216.

When the pump is on, the parallel entry enable line 218 of the counters U28, 96, and U29, 98, is high, passing the fixed binary number to the outputs of the counters and to the R-2R ladder network, providing a reference voltage for the comparator U36, 94. The output of U36 is low until the cuff pressure exceeds the value from U28 and U29 corresponding to the fixed binary number. When the cuff pressure exceeds 180 mmHg, the comparator U36 changes its state and stops the pump through the OR gate U13A, 120 of FIG. 3, and the flip-flop U3B, 108 of FIG. 3. The output of the comparator 94 of FIG. 5 also resets the flip-flop U37A, 212 of FIG. 5, connecting the parallel inputs to the binary adders U34, 220, and U35, 222, which are hard-wired to add 20 mmHg to the value input. The pump being stopped, the parallel entry line enable line 218 is low, causing the analog-to-digital converter to operate as described above. When a pulse occurs at the systolic enable line 224 of FIG. 5, the then-present output of the analog-to-digital converter is stored in the systolic register U30, 200, and in the latches U32, 226, and U33, 228. The value stored in the latches 226, 228 is one set of inputs to the adders 220, 222. The hard-wired fixed value of 20 mmHg is added to the input value by the adders and the result is then passed by the multiplex gates 214, 216 to the parallel inputs of the counters 96, 98. This assures that on succeeding cycles the cuff pressure will be 20 mmHg above the preceding systolic measurement.

If a change in systolic blood pressure in excess of 20 mmHg occurs, a K-sound will follow the first heartbeat. The K-pulse travels through the NAND gate inverter U22C, 230 of FIG. 3, and NOR gate U20 to set the flip-flop U3B, 108 of FIG. 3, the pump power control, and the cuff pressure is thereby increased 20 mmHg. Three $\overline{K}$-pulses must occur in succession before the measurement cycle is permitted to continue. After the three $\overline{K}$-pulses occur, the NOR gate U20 is disabled by the counter U23, 232 of FIG. 3, and any subsequent K-pulses cannot restart the pump.

If the addition by the adders 220, 222 of FIG. 5 of 20 mmHg to the previous systolic pressure results in overflow, the high order carryout from the adder U34, 220 of FIG. 5, puts the multiplex gates U26, 214, and U27, 216 in a high impedance state. In this state, the parallel input lines of the counters U28, U29, 96 and 98, are all now held at binary ones (thereby representing the maximum pressure of 255 mmHg) by the eight pull-up resistors 234, and cuff inflation stops when this maximum pressure has been reached.

Although primarily intended for use where recording of heart-related data is desired over extended periods of time, the BPM System of the present invention includes the capability of presenting some types of data as soon as it is obtained. This capability is useful in proofing the accuracy and proper application and operation of the BPM System, and additionally provides a convenient means for the physician, or a patient under the physician's orders, to determine the current value of the blood pressure.

Thus, provision is made, as shown in FIG. 6d for amplifying the K-sounds and presenting them at a connector 505 so that the K-sounds can be heard by use of an earphone or other device.

To permit the most recently measured values of systolic and diastolic blood pressure to be read out without delay, the digital display circuit 76 of FIG. 2 is provided. A schematic diagram of this circuit is presented in FIG. 10, which will now be discussed.

As described above, in the BPM System, digital data is handled in eight-bit binary-weighted format. (Bit $0=2^0$; bit $1=2^1$; bit $2=2^2$, etc.) This data format would be difficult for physicians or patients to interpret rapidly and correctly, and therefore is not desirable for direct display. Further, the binary values from the analog-to-digital converter 54 of FIG. 2 are generally constantly changing at an eight-kHz rate, reflecting the current cuff pressure and lowest digit dither, and would therefore be impossible to follow visually. As will be seen below, the digital readout of FIG. 10 solves these problems by translating the binary-weighted values into binary coded decimal form and presents the information as two three-digit decimal numbers which are numerically equal to the systolic and diastolic blood pressures in mmHg. The last-measured values of the blood pressure are electronically latched into the displays so that the information is presented on demand in an easily-read flicker-free form. The last-measured values are therefore available for display upon manual activation of a push button switch and the values are automatically cleared when a new measurement has been made. Leading zeros, if any, are blanked from the display electronically for ease of reading.

The eight-bit binary-weighted pressure representation present in the analog-to-digital converter, 54 of FIG. 2, are brought into the digital display circuit on the lines 236 of FIG. 10. The integrated circuits U1 and U2 are buffer amplifiers to prevent loading of the analog-to-digital converter electronics. The systolic enable line 224 and the diastolic enable line 225 of FIGS. 3 and 5 are also brought in and buffered, as shown in FIG. 10.

The binary data lines are then connected to the data translators U5, U6 and U7, 238, 240 and 242 respectively. These are read-only memories which are connected to make the conversion from binary-weighted format to three-digit binary coded decimal format. The digital readouts U8 through U13, designated generally by reference numeral 503, have built-in latches to hold the data entered, and are commercially available. A pulse on the systolic enable line 224 enters the binary-coded decimal data produced by the data translators 238, 240, 242 into the systolic pressure displays U8, U9 and U10. A pulse on the diastolic enable line 225 enters the binary coded decimal data into the diastolic displays U11, U12 and U13. Because of the built-in latches, once the data has been entered it remains displayed until another enable pulse arrives.

The data translators 238, 240, 242 are commercially available and are constructed so that a high level on pin 15 results in all the outputs being driven to the logic 1 state. Each of the binary digits displayed is represented by binary signals on four parallel lines which could, of course, provide representation for numbers as large as sixteen. Since each of the digital read-outs U8–U13 can display only ten different decimal digits, the surplus representation ability of the four lines carrying data to each readout can be used for control purposes. The digital readouts U8–U13 used in the circuit are blanked when presented with a binary number on the four input lines, representing the number 15.

When there is a pulse on neither the systolic enable line 224, nor the diastolic enable line 225, the NOR gate U4A, 244, senses this no-signal condition, and the output of U4A goes high driving the data translators U5, U6 and U7 into the logic 1 state. The data translators then present each of the displays U8–U13 with a binary number equivalent to 15. Thus, unless one of the enabling pulses is occurring, the inputs presented to the display units U8–U13 will each equal 15. This "15" input is then read into the display units U8–U13 by closing the reset switch 246 which, through the inverters U3C and U3D brings the lines 248, 250 low entering the all-ones input to the display units thereby blanking them.

The NOR gate U4B, 252, senses the absence of a leading digit, and if this occurs during an enable pulse, the NOR gate 254 produces through the inverter U3E a signal which is applied to the leading digits U8 and U11 of the display to blank those digits only.

As described above in connection with the system block diagram of FIG. 2, the serial DPWM data on line 62 is presented to the portable magnetic tape recorder 16, which can accommodate up to twenty-six hours of data. FIG. 7 is a schematic diagram of the data-processing electronic circuitry of the tape recorder 16.

As mentioned above, the tape recorder 16 has the capability of simultaneously recording data on two tracks of a magnetic tape. Accordingly, the schematic diagram of FIG. 7 may be regarded as broadly including two channels, shown in the upper and lower portions of FIG. 7, respectively. As shown in FIG. 7, these two channels have similar configurations, with exceptions. Regarding the exceptions, it will be noted that the second channel includes the event marker circuitry 256 and the multiplex circuit 258. A common power supply 260 supplies both of the channels.

Signals from the ECG electrodes 18 of FIG. 2 are conveyed to the tape recorder 16 by the cable 22 of FIG. 2. The leads of the first channel of ECG signals enter the recorder electronics of FIG. 7 at pins 1 and 2 denoted generally at 262 in FIG. 7, while the signals from the second ECG channel are applied at pins 4 and 5 which are shown generally at 264 of FIG. 7. The ECG signals in the first channel are amplified by the amplifier 266 which has a gain of 10, and which is connected to the amplifier 268 by a pre-emphasis network 270. The capacitors C2, C3, 272, provide dc isolation between the amplifier stages. The amplifier 268 has a gain of 12. The sawtooth generator 274 provides a linear sawtooth signal having a predetermined repetition frequency. The output of the amplifier 268 is compared with the sawtooth signal generated by means of the comparator 276. Thus, an input is received at the inverting buffer U4, 278, only when the output of the amplifier 268 exceeds the output of the sawtooth generator 274. Accordingly, the output of the inverting buffer 278 is a pulse-width modulated representation of the output of the amplifier 268. This pulse-width modulated representation is then applied to the head driver circuit 280 which in turn drives the recording head 282 that records one of the tracks on the magnetic tape.

The second channel of the recorder includes a first amplifier 284, coupled through the pre-emphasis network 286 to a second stage of amplification 288. The output of the second stage of amplification 288 is applied to the multiplexer 258 on the line 290. The multiplexer 258 under the control of a signal on the line 292 selectively applies to its output line 294 either the output ECG signal on the line 290, the blood pressure data on the line 296, or the event marker signal generated by the event marker circuit 256.

In the preferred embodiment of the tape recorder 16, the highest priority for recording is given to the B.P.M. System data input on line 296. The second priority is given to the event marker signal, and if neither blood pressure data nor an event marker signal is present, the ECG signal on the line 290 will be recorded. Because the duration of the event marker is greater than the time required for reading the serial pressure data, a fragment of the normal event marker signal will be recorded even if it is interrupted by the higher-priority blood pressure data. The ECG signal is a continuous and somewhat repetitious signal, while the blood pressure data would normally be read out only during an interval of less than one second at intervals of fifteen minutes normally. Hence, the priority scheme chosen in the preferred embodiment is a reasonable and practical way of implementing the recording of these three types of signals on a single track of the magnetic tape.

Whichever one of the three signals is being passed to the output line 294 by the multiplexer circuit 258 under control of the control signals on the line 292, is applied to the comparator 298 for comparison with the output of the saw-tooth wave generator 300 to produce a pulse-width modulated signal on the line 302 for application to the head-driver circuit 304 for use in driving the magnetic head 306, which records the second track of data on the magnetic tape.

Referring back to FIG. 2, the magnetic tape 74 produced by the portable tape recorder 16 is removed from the tape recorder after the desired amount of data has been recorded, and inserted into an electrocardiographic computer 32 of FIG. 2 for playback, analysis, and plotting of the data recorded. The electrocardiographic computer 32 is generally similar to that disclosed in the co-pending U.S. patent application Ser. No. 717,651 filed Aug. 25, 1976, and invented by I. R. Cherry and D. L. Anderson. The electrocardiographic computer 32 of the present invention differs from that disclosed in the aforementioned application in that a data decoder 86 and a multiplexer gate 88 of FIG. 2 have been added to permit the three types of signals selectively recorded on the tape to be decoded and selectively applied to the plotter 82 portion of the electrocardiographic computer 32.

FIG. 8 is a schematic diagram showing a preferred embodiment of the data decoder 86 used with the B.P.M. System of the present invention. It will be noted that the data decoder 86 operates only on the signals that were stored on the second channel or track of the tape. As described above, at any moment the signal on the second track of the tape might represent ECG signals, an event marker signal, or blood pressure data generated by the BPM System. The data decoder 86, in effect, sorts out these signals as will be described below.

The saw-tooth generators 274, 300 of FIG. 7 operate at fixed repetition and frequencies in the range 2.5–5.0 KHz. This is a much higher frequency than either the ECG signals, the event-marker signals, or the serial pressure data signal, the latter being read at a rate of 32 Hz. The recording heads 282, 306 of FIG. 7 do not respond to frequencies as high as that used for the saw-tooth generators and hence the signals impressed on the magnetic tape are substantially analog representations of the ECG signal, the event-marker signal, and the blood pressure data signal. As a result, when the tape is played back, signals are generated which are analog representations of the ECG signal, the event-marker signal and the blood pressure signal. This in turn, enables the data decoder of FIG. 8 to sort out the blood pressure data signals, when they are present, on the basis of the analog characteristic of those signals.

As described above, in connection with FIG. 5, a readout of systolic and diastolic blood pressure data is in the form of sixteen serial binary bits. These binary bits are recorded on the tape in one half-second and the sixteen bit data group is preceded and followed by ⅛ second of zero level "quiet" time to insure that ECG signals or event-marker signals will not interfere with the digital information. Further, in a preferred embodiment the digital data signal applied to the comparator 298 of FIG. 7 is of the order of five volts, while the saw-tooth signal with which it is compared is on the order of 1.8 volts. As a result, the data signals are recorded with great amplitude on the magnetic tape.

Essentially, the data decoder recognizes the blood pressure data signal among the signals provided by the tape playback unit 78 of FIG. 2 by the fact that the data signal always consists of exactly sixteen pulses in a sequence which occurs at a 32 Hz rate. As will be described below, this is accomplished by a clock and a resettable counter arrangement which will not respond unless exactly sixteen pulses occur at the specified rate.

In the following description only the channel 2 data, that is, the signal from the track of the magnetic tape which includes the superimposed ECG signals, event-marker signals and blood pressure data signals is applied to the data decoder, since there is no need to decode the ECG data on the other track of the tape.

The data decoder is enabled only when the tape playback unit 78 or FIG. 2 is in either the X60 of X120 playback modes. Under these conditions, one input of NAND gate U3A, 308 of FIG. 8, will be low. A low signal results on the enable line 310, and the multiplex gate U6, 332, passes gating signals. The gating rate is determined by the input to pin 1 of the multiplex gate U6, 332: a low level for X60, and a high level for X120.

The signal from the multiplexed track of the magnetic tape as obtained by the tape playback unit 78 of FIG. 2, is applied to the decoder through the capacitor C1, 314 of FIG. 8, which rejects low frequencies and prevents dc drift. The signal is then applied to the full wave rectifier 316 which is adjusted so that the input signal must exceed one volt in magnitude before any signal is applied to the amplifier 318, thereby eliminating low voltage signals and noise. The amplifier 318 has a gain of 100 and produces a series of positive pulses at its output. These pulses are of the order of five volts in a preferred embodiment.

The pulses generated by the amplifier 318 are then applied to a Schmidt trigger 320 which inverts the pulses and standardizes them. The pulses forming network 322 converts the negative-going transitions to narrow positive pulses on the line 324 and also converts the positive-going transitions to narrow positive pulses output on the line 326.

The pulses on line 324 trigger the one-shot multivibrators U4, 328, and U5, 330 to start gate signals. In the X60 mode, signals from the one-shot multivibrator 328 are passed, and in the X120 mode, signals from the one-shot multivibrator 330 are passed by the multiplex gate 332. In the X60 playback mode, the Q output of U4A, on line 334, is passed through multiplex gate 332 to NAND gate U3D, 336, the $\overline{Q}$ output of U4A on line 338 is passed through the multiplex gate 332 to the NAND gate U3C, 340, the $\overline{Q}$ output of U4B on the line 342 is routed to the NAND gate U3D, 336, while the Q output of U4B on the line 344 is routed through the NAND gate U3B, 346. When the X120 playback mode is used, the outputs of the multivibrator 330, U5, are connected analogously to those of the multivibrator 328.

When no input signal is detected, the outputs of both U4A and U4B are in the one (high) state. This causes the output of the NAND gate 336 to be low and the output of the NAND gate 336 propagates through the NOR gates U8B, 348, and U8D, 350, and through the NAND gate U7C, 352, to reset the flip-flop U10, 354, and the counter U9, 356.

The leading edge of an incoming pulse train on line 324 will initiate a timing cycle in U4A, resulting in its Q output on the line 338 going high and its $\overline{Q}$ output on the line 334 becoming low. The low level of $\overline{Q}$ on the line 334 operates through the NAND gate U3D, 336, to release the reset conditions on the counter U9, 356, and the flip-flop U10, 354. If a pulse occurs on the line 326 during the time when the Q output of U4A on the line 338 is high, that pulse will pass the NAND gate U3C, 340, and the inverter U2F to set the flip-flop U10, 354. This represents a data "one". If no pulse occurs during the time when the Q output of U4A is high, the flip-flop U10, 354, is left in the data "zero" condition. Pulses from the pulse forming network 322 will not affect the duration of the one-shot multivibrator U4A.

When the Q output of U4A returns to the low level, the transition triggers U4B into conduction. The $\overline{Q}$ output of U4B is then low and when it is applied through U3D, 336, it prevents the counter U9, 356 and the flip-flop U10, 354, from being reset. The resistor R11, 358, and the capacitor C8, 360, absorb the narrow pulse that occurs between when the $\overline{Q}$ output of U4A reverts to the high state and when the $\overline{Q}$ output of U4B reaches the low state, and thereby prevents a reset from occurring during that interval. A pulse on the line 326 occurring during the time when the Q output of U4B is high is decoded by the NAND gate U3B, 346 as a clock transition. The pulse through the NOR gate U8A, 362, increments the counter U9, 356, transfers the state of the flip-flop U10, 354, into the shift register U11, 364, and resets the flip-flop U10 to the data "zero" state.

The next pulse from the pulse forming network 322 on the line 324 will start another cycle in similar fashion until eight pulses have been counted by the counter U9, 356. The rise of the eight-count output of U9 (pin 6) is fed through the capacitor C9, to the NAND gate U7B, 366, and through the NAND gate U15A, 368, to the shift register 364, transferring the contents of its shift register to its storage register. These eight bits represent the systolic pressure measurement. After eight more clock pulses, the sixteen-count output (pin 5) of the counter 356 goes high. If the $\overline{Q}$ outputs of both U4A and U4B are high, an "end-of-data" condition is decoded and the output of the NOR gate U8C, 388, goes to Logic 1 indicating a "data valid" condition. Further, clock pulses to the counter U9 and the shift register U11, 364, are disabled.

If another clock pulse occurs before both the output of U4A and U4B go high, the counter U9, 356, is incremented to show a count of 17. At this count, the output of the NAND gate U7D, 372, drops, causing the output of the NAND gate U7C 352 to rise, resetting the counter U9, 356, and the flip-flop U10, 354. In this case, the "data valid" line 374 never rises.

When the "data valid line" 374 rises, the one-shot multivibrators U13A, 376, and U14B, 378, are triggered. The $\overline{Q}$ output of U13A is used to prevent a reset from occurring while data is transferred to the output of the decoder. The Q output of U13A, 376, controls the multiplex gate U18, 380 of FIG. 9. When the Q output of U13A is high, the heartrate meter is disconnected and the output of the amplifier U17A, 382 of FIG. 8, is connected to the output terminal of the heartrate trend computer. For 0.5 seconds, the first eight bits stored in the storage register of the shift register U11, 364, are converted by the digital-to-analog computer U12, 384, to an analog voltage and put on the trend chart. After 0.5 seconds has elapsed, a pulse from the one-shot U14B, 378, transmitted through the NAND gate U15A, 368, causes the second eight bits in the storage register portion of the shift register U11 to be stored in its output latch. This data is again converted by the digital-to-analog converter U12, U17 to analog form and recorded on the trend chart.

After 1.0 seconds have elapsed, the Q output of the one-shot U13A, 376, goes low, returning the trend output to the heartrate meter. The one-shot U13B, 386, is triggered and it applies a pulse to the NOR gate U8D, 350, which resets the counter U9, 356, and the flip-flop 354. When pin 5 of the counter U9, 356, drops to zero, the output of the NOR gate U8C, 388, drops, ending the data cycle.

Figure 15:
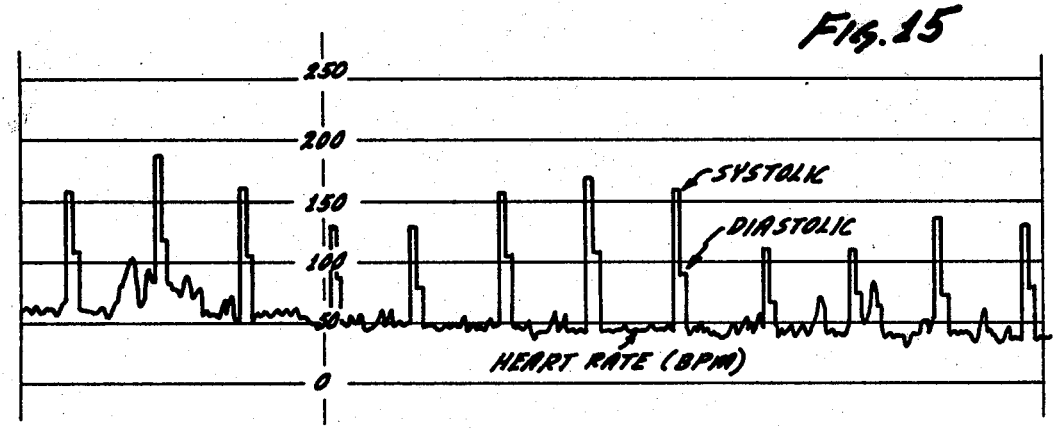
FIG. 15 is a facsimile of the plotted output obtained when the B.P.M. System of the present invention is used; and, FIG. 16 is a perspective view showing panel connections and controls to a preferred embodiment of the present invention.

The output of the digital-to-analog converter U12, U17 is scaled to correspond to the zero-to-250 scale on the heart rate trend chart. Blood pressure may now be read directly from a chart, a preferred embodiment of which is shown in facsimile form in FIG. 15. The blood pressure readings appear as two pedestals, each 1 mm in width on the trend recording, and are easily distinguished from the heart rate data.

In another embodiment, the blood pressure readings are printed in numerical or alpha-numerical form on the heart rate trend chart.

FIG. 9 is a schematic diagram of the heart rate trend computer 80 of FIG. 2. The multiplex gate 88 of FIG. 2 is shown as the multiplex gate 380 of FIG. 9. Depending upon the playback speed used, the incoming ECG data on line 390 or 392 is applied to a one-shot multivibrator 394 or 396, respectively, which generates a standardized pulse at the occurrence of each recognizable R-peak of the ECG signal, i.e., at each heartbeat. The standardized pulses thus generated are applied to a pulse-averaging low-pass filter 398 which converts the incoming pulse train to a smoothly varying analog signal representing the pulse rate, on the line 400. This pulse rate signal is applied through the buffer amplifier 402 to the multiplex gate 380, which passes it to the output terminal on the line 404, except when blood pressure data is being read out. The blood pressure data on the line 406 of FIG. 9 is the same data as on the similarly numbered line 406 of FIG. 8. In response to a control signal on the line 408 of FIG. 9 (also shown as line 408 in FIG. 8) the multiplex gate 380 disconnects the output of the buffer amplifier 402 from the gate output 404 and instead connects the blood pressure signal on the line 406 to the gate output 404. Except for the implementation of this feature by way of the multiplex gate 380, the heart rate trend computer shown in FIG. 9 is substantially similar to that disclosed in the above-referenced U.S. application Ser. No. 717,651, which also describes the plotter 88 of FIG. 2.

The operation of the B.P.M. System of the present invention can be summarized conveniently by reference to the logical flow diagram of FIG. 11. That diagram generally describes the operation of the B.P.M. System 10 of FIG. 2. Normally, the chart is entered at the manual operation symbol 412 which represents the start/-stop switch S1, 126 of FIG. 3. Assuming the switch was placed in the start position, the counters will be initialized, the valve closed and the pump started, as indicated at the initialization block 414 of FIG. 11. A test is continually made, as indicated by the decision symbol 416, to determine whether the cuff pressure has reached the pre-set value of the initial inflation pressure. This is determined by the comparator U36, 94 of FIG. 5. If the cuff pressure has reached the preset value the pump is stopped and the initial inflation phase of the cycle of operation is completed and the measurement phase is begun, as indicated by the operation symbol 418.

If the cuff pressure has not reached the preset initial inflation pressure, a test is made to determine whether sixteen seconds have elapsed since the pump was turned on. This is indicated by decision block 420 and determined by the signal on the line 118 of FIG. 3.

After the initial inflation pressure has been reached, the measurement phase is begun with the decision symbol 422 which involves the question of whether an R-wave has been detected as yet in the cycle. If no R-wave has been detected and if more than two seconds have elapsed (decision symbol 424) the $\overline{R}$ flip-flop is set and the system goes into the extended gate mode discussed above in connection with FIG. 4 and in which the K gate is extended to a full two seconds. If at the decision symbol 422 an R-wave is detected, the K gate U19D, 148 of FIG. 4, is set, as indicated by the operation symbol 426. Thus, either an extended K gate or the regular K gate is established before the decision block 428 is entered. If a K-sound has occurred during the duration of the K-gate, the cuff pressure is reduced by approximately 3 mmHg as indicated by operation symbol 430. A K-sound having occurred during the gate, the circuit next tests to determine if the initial $\overline{K}$ flag embodied in U23, 232 of FIG. 3, has been set, the test being indicated in FIG. 11 by the decision block 432. If the initial $\overline{K}$ flag has not been set, it means that the preset initial inflation pressure was inadvertently below the systolic blood pressure and accordingly the initial inflation pressure is increased by 20 mmHg, as shown by operation symbol 434 and a completely new cycle of operation is initiated as the flow chart jumps to the junction 436. On the other hand, returning to the decision block 432 if the initial $\overline{K}$ flag had been set, the diastolic $\overline{K}$ counter U7, 174 of FIG. 3, is reset as indicated by operation symbol 438 and then a test is performed to determine whether the diastolic gate is open, as determined by the Q output of U8B, 172 of FIG. 3. If the diastolic gate was open, it means that a systolic pressure had already been identified, and the system stores the current pressure as a potential diastolic pressure, as indicated by operation symbol 440, and then awaits the arrival of the next R-wave. On the other hand, if the diastolic gate is not open when the decision symbol 442 is reached, the system stores the then-current pressure as the systolic pressure in the systolic register 200 of FIG. 5, adds 20 mmHg to the systolic pressure stored, by means of the adders 220, 222 of FIG. 5, for use as the initial inflation pressure in the succeeding cycle of operation, and finally, the system opens the diastolic gate, all of the above operations being included within the operation symbol 444 of FIG. 11. Thereafter, the system awaits arrival of the next R-wave.

Returning now to the decision symbol 428, if no K-sound occurred during the K gate, the cuff pressure is reduced by 3 mmHg as indicated at operation block 446, and the process continues to decision block 448 which is a test for whether the initial $\overline{K}$ flag has been set. This is implemented as mentioned above through the counter U23, 232 of FIG. 3.

If the initial $\overline{K}$ flag has not been set previously, the initial $\overline{K}$ counter U23 of FIG. 3 is incremented as indicated by operation symbol 450 and a test is performed as indicated by the decision symbol 452, to determine whether the initial $\overline{K}$ count on the counter U23 is equal to 3. If the count has not reached 3, the system awaits the next R-wave but if the initial count has reached 3, then the initial $\overline{K}$ flag is set as indicated by the operation block 454, and then the system awaits the arrival of the next R-wave.

Once the initial $\overline{K}$ flag has been set, the flow chart will branch from the decision block 448 to the decision block 456. As indicated by that block, a test is made to determine whether more than one K-sound has been heard. This test is based on the states of the flip-flops U8A and U8B, 170, 172 of FIG. 3. If there has been only one K-sound heard, then the diastolic gate is closed and the systolic gate is enabled, as indicated by the operation block 458. These functions are implemented through the flip-flops U8 and the AND gates U11A and U11B, all of FIG. 3. After these operations are completed the system awaits arrival of the next R-wave.

Returning to the decision block 456, if more than one K-sound has been obtained in succession following the setting of the initial $\overline{K}$ flag, the diastolic $\overline{K}$ counter U7, 174 of FIG. 3, is incremented in accordance with operation block 460, and a test is made to determine if the diastolic count on the counter U7 has reached 3. That test is shown as decision block 462.

If the count has not reached 3, the system merely awaits the arrival of the next R-wave. On the other hand, if the count has reached 3, the data output is enabled as indicated by the operation block 464, and then the cuff pressure is relieved, ending the cycle of operation as indicated by the operation symbol 466, before the entire cycle of operation is initiated again by the fifteen-minute timer. The operations indicated in the block 466 can also be initiated by activation of the stop switch 412 or independently by the two-minute timer as indicated by the block 468, and as implemented by the counter U2 of FIG. 3.

Figure 11:
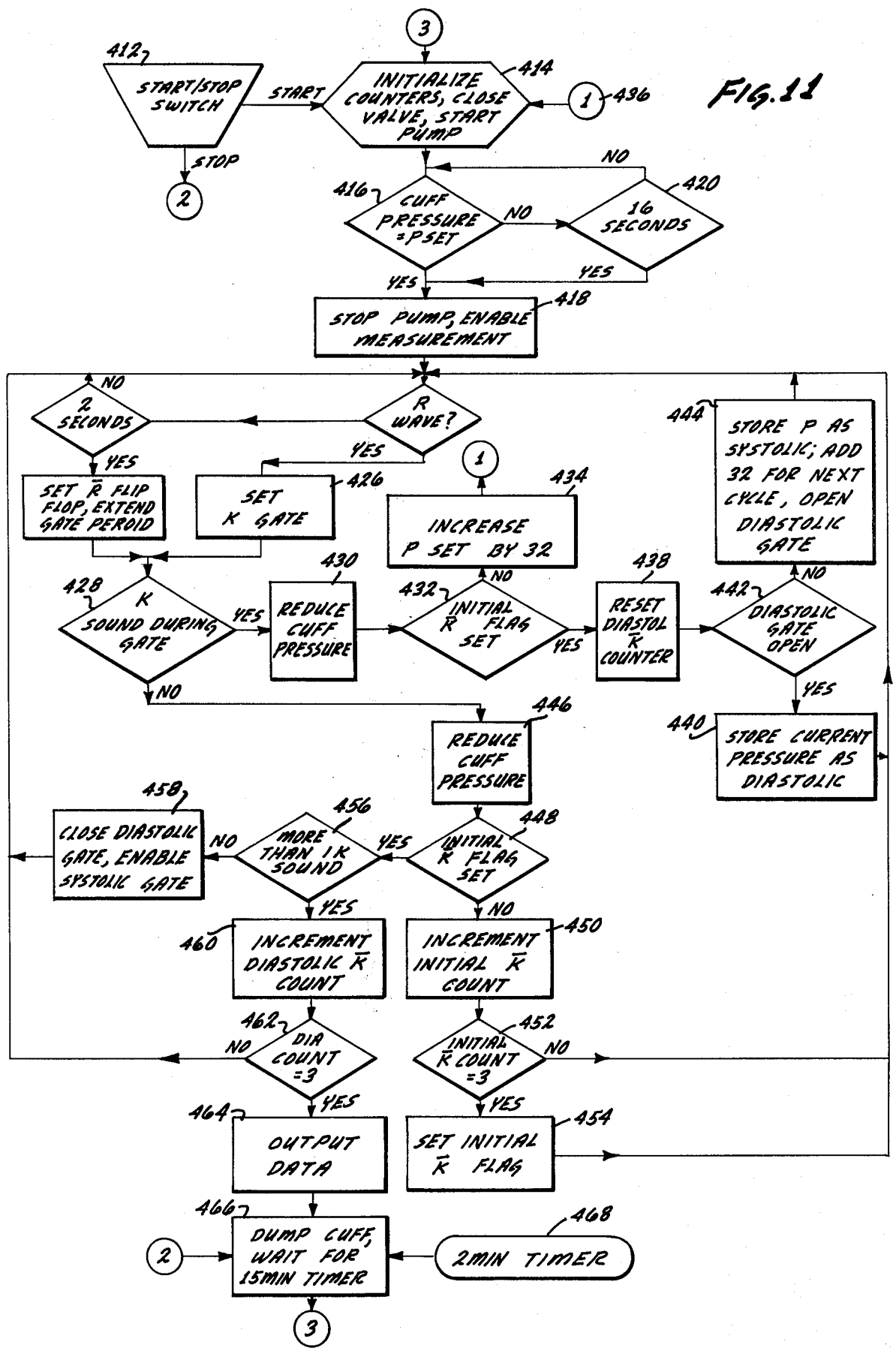
FIG. 11 is a logical flow chart of a preferred embodiment of the present invention.
Figure 13:
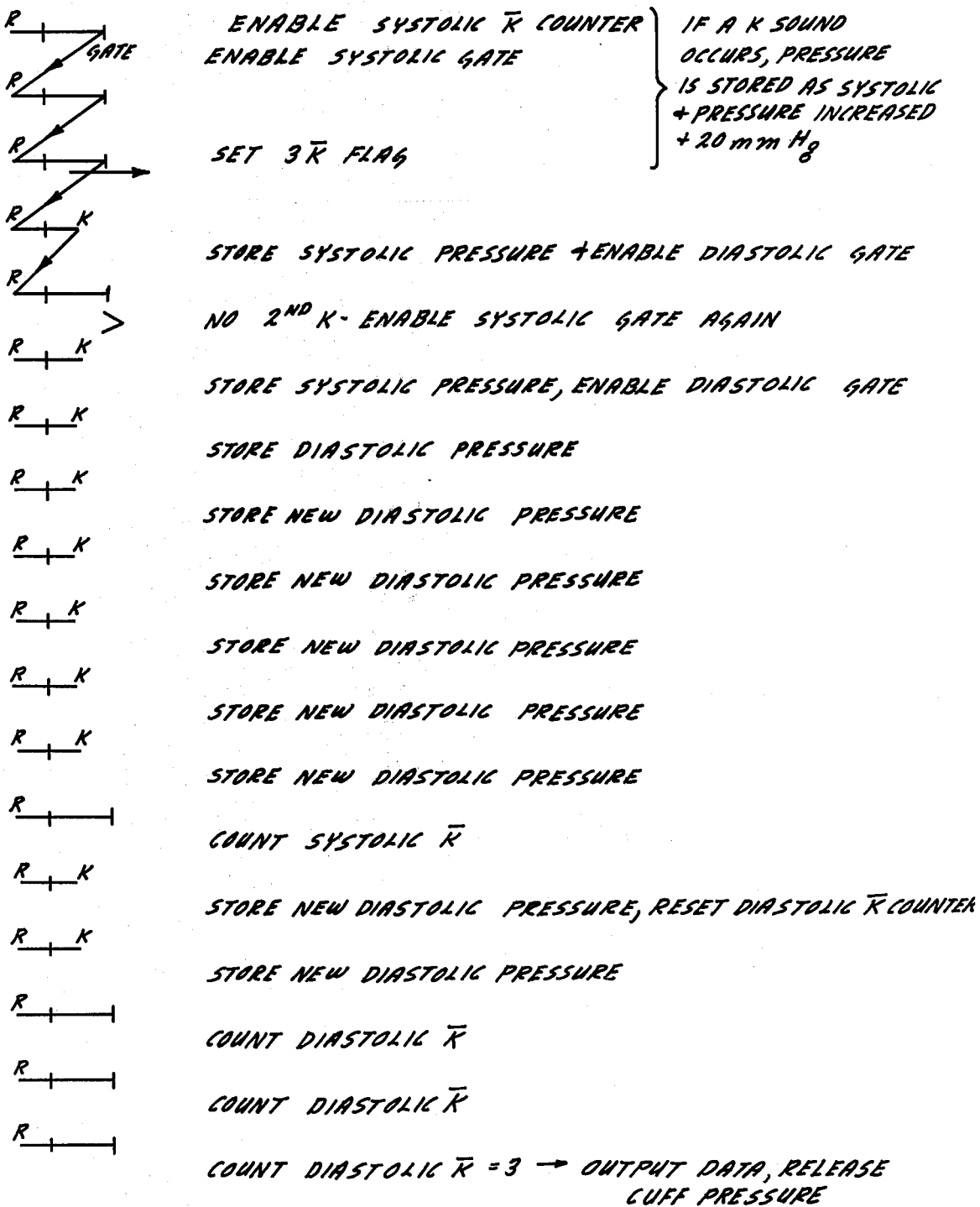
FIG. 13 is a diagram illustrating the sequence of heartbeats, K-sounds, and operations performed in the B.P.M. System of the present invention.

The various events that occur in the course of the flow chart of FIG. 11 in the course of a normal measurement cycle in which the initial inflation pressure was greater than the systolic pressure and in which the pulse rate is normal, are shown in FIG. 13. In that figure, the time of occurrence of successive R-waves is indicated by successive lines vertically in the figure. The commencement and cessation of the K-sounds are also shown.

Figure 16:
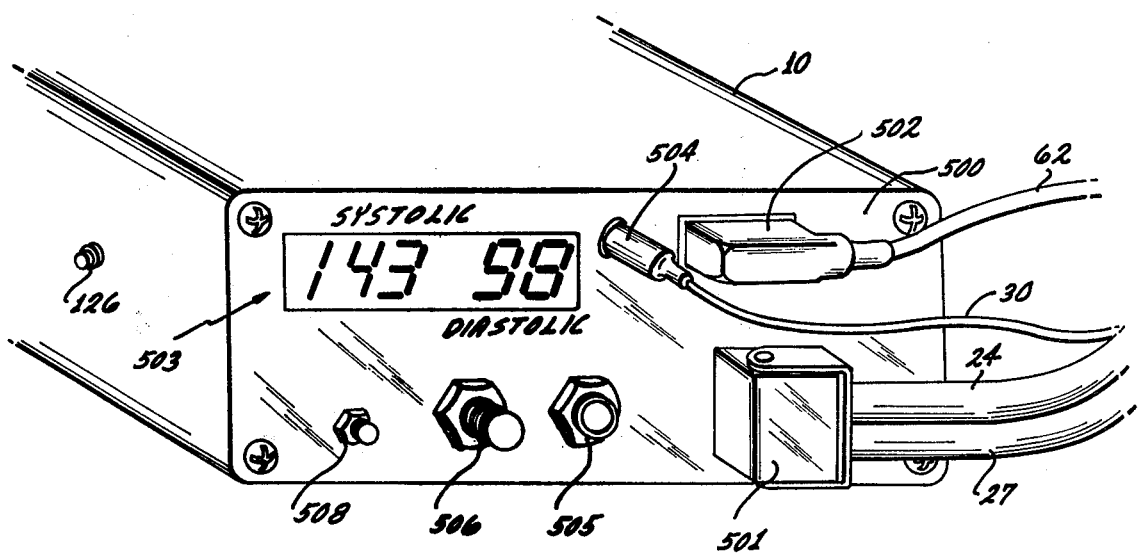

FIG. 16 is a perspective view of the panel connections and controls in a preferred embodiment of the BPM System. The pump, valve, pressure transducer, battery power supply, and display are all packaged, along with the circuitry, in the relatively small housing of the BPM System 10 of FIG. 1. The hoses 24, 27 (also shown in FIG. 2) extend from the hose connector 501 to the cuff. Likewise, the microphone cable 30 (shown in FIG. 1) extends from the connector 504 to the microphone, which is located adjacent the cuff. The recorder cable 62 carries the interconnections between the recorder (16 of FIG. 1) and the BPM System. The start-/stop switch 126 permits manual intervention in the normally automatic operation of the BPM System to initiate or terminate a cycle of operation at any time. The digital display 503 (also shown in FIG. 10) is activated by the display switch 508 to show the most recent systolic and diastolic blood pressure values, which remain stored in the circuitry. The connector 505 (also shown in FIG. 6d) permits the physician to listen to the sounds produced by the microphone 28 of FIG. 1. A connector 506 is provided to permit attachment of an external mercury column for calibration purposes. Thus, all communication between the BPM System and the rest of the world passes through the panel 500.

Thus, there has been described an apparatus for the long-term ambulatory monitoring of blood pressure by an auscultatory method, employing a pressurizable cuff and requiring no intervention by the patient. The patient's heartbeats are sensed by ECG electrodes attached to his body and a microphone is used to sense the Korotkow sounds as the pressure in the cuff is varied automatically under the influence of the apparatus.

The presence or absence of a Korotkow sound within a preset interval following each heartbeat is used in determining when the cuff pressure equals successively the systolic and diastolic pressures. Those pressures are determined in each cycle of operation and are recorded on a continuously-running portable tape recorder, along with the ECG signals.

In each cycle of operation, the initial pressure to which the cuff is inflated is based on the greatest pressure measured in the immediately preceding cycle. The pressure in the inflated cuff is thereafter stepped downward in small discrete decrements triggered by successive heartbeats during the measurement phase of each cycle. After both the systolic and diastolic pressures have been determined, the remaining cuff pressure is vented through the same valve that was used to produce the stepwise pressure reduction.

After a number of cycles of operation have been recorded on the magnetic tape, the tape is removed from the portable tape recorder and may later be inserted into an analyzer for high-speed playback and automated plotting of the patient's heartrate and corresponding blood pressure readings on a common chart.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A portable apparatus for long-term ambulatory monitoring and recording of a patient's systolic and diastolic blood pressure by the auscultatory method, requiring no intervention by the patient and comprising in combination:

an inflatable cuff affixable to the patient;

a source of fluid under pressure for inflating said cuff to an initial inflation pressure greater than the patient's systolic blood pressure during an initial phase of each cycle of operation in response to an applied inflation signal, and thereafter for remaining sealed off from the cuff during the remainder of each cycle of operation;

a pressure transducer for sensing the pressure of the fluid in said cuff and for generating a pressure signal representative of the pressure;

a valve connected to the cuff and having a normal first state in which it vents said cuff to a region of lower pressure, and alterable by applied control signals to a second state in which it connects said cuff to said source of fluid;

a valve control circuit connected to said valve and generating the control signals applied to said valve to selectively control its state in response to a stored initial inflation pressure signal stored in said valve control circuit and to the pressure signal generated by said pressure transducer to cause said cuff to be inflated to the stored initial inflation pressure during the initial phase of each cycle of operation, the initial inflation pressure signal for the first cycle of operation being preset and the initial inflation pressure signal for each subsequent cycle of operation being determined by said valve control circuit from the greatest pressure measured by said portable apparatus in the immediately preceding cycle of operation and retained in storage by said valve control circuit, said valve control circuit responding to stepping signals generated and applied after the initial inflation phase of each cycle of operation to initiate the control signals applied to said valve to selectively and intermittently vent said cuff to a region of lower pressure momentarily producing an abrupt decrease of the cuff pressure by a constant predetermined decrement upon the occurrence of each of said stepping signals until the cuff pressure has been reduced through a series of constant pressure decrements from the initial inflation pressure greater than the patient's systolic blood pressure to a final cuff pressure less than the patient's diastolic blood pressure;

a K-sound transducer positioned on the patient in relation to said inflatable cuff for sensing the patient's K-sounds during the intervals when the cuff pressure is constant between successive pressure decrements and for generating a K-sound signal representative of the K-sounds;

a discrimination circuit responsive to the K-sound signal for identifying the first and last of the K-sounds sensed by said K-sound transducer in each cycle of operation and responsive to the pressure signal for producing an output data signal representing the systolic and diastolic pressures sensed by said pressure transducer at the time of occurrence within each cycle of operation of the first and last K-sounds respectively, said discrimination circuit connected to said valve control circuit and producing the stepping signals and applying the stepping signals to said valve control circuit.

2. The apparatus of claim 1, further comprising a pair of ECG electrodes for sensing the patient's electrocardial potentials and for providing an ECG signal representative thereof, and wherein said discrimination circuit is responsive to the ECG signal to generate the stepping signal applied to said valve control circuit.

3. The apparatus of claim 2 wherein said discrimination circuit includes means for determining when the patient's R-waves can be recognized in said ECG signal, and when the R-waves can be recognized said discrimination circuit generates and applies to said valve control circuit a stepping signal in timed relation to each R-wave, whereby the cuff pressure is reduced in a stepwise manner, the successive decrements of pressure being paced by successive R-waves.

4. The apparatus of claim 3 wherein said means determines when the patient's R-waves can be recognized in said ECG signal, and when the R-waves cannot be recognized said discrimination circuit generates and applies to said valve control circuit stepping signals having a constant repetition frequency, whereby the cuff pressure is reduced in a stepwise manner, the successive decrements of pressure being equally spaced in time.

5. The apparatus of claim 2 wherein said discrimination circuit including means for determining when the patient's R-waves can be recognized in said ECG signal, and if the R-waves cannot be recognized said discrimination circuit generates and applies to said valve control circuit stepping signals having a constant repetition frequency, whereby the cuff pressure is reduced in a stepwise manner, the successive decrements of pressure being equally spaced in time.

6. The apparatus of claim 1 wherein said discrimination circuit, upon detecting the occurrence of a K-sound within a limited defined time interval after the end of the initial inflation phase of a cycle, generates a signal for application to said valve control circuit, said valve control circuit including means responsive to said signal for terminating the measurement cycle for augmenting the stored initial inflation pressure signal by a predetermined increment and for generating an inflation signal to increase the cuff pressure to the pressure represented by the augmented initial inflation pressure signal.

7. In an apparatus for monitoring a patient's blood pressure by the auscultatory method, of the type including an inflatable cuff for affixation to the patient, a source of fluid under pressure for inflating the cuff to an initial inflation pressure during an initial phase of each cycle of operation in response to an applied inflation signal, and thereafter for remaining sealed off from the cuff during the remainder of each cycle of operation, further including a pressure transducer for sensing the pressure of the fluid in the cuff and for generating a pressure signal representative of the pressure, further including a valve connected to the cuff and having a normal first state in which it vents the cuff to a region of lower pressure, and alterable by applied control signals to a second state in which it connects the cuff to the source of fluid, further including a K-sound transducer positioned on the patient in relation to the inflatable cuff for sensing the patient's K-sounds and for generating a K-sound signal representative of the K-sounds, further including a pair of ECG electrodes for sensing the patient's electrocardial potentials and for providing an ECG signal representative thereof, and further including a discrimination circuit responsive to the K-sound signal and to the ECG signal for identifying the first and last of the K-sounds sensed by the K-sound transducer in each cycle of operation and responsive to the pressure signal for producing an output data signal representing the systolic and diastolic pressures sensed by the pressure transducer at the time of occurrence within each cycle of operation of the first and last K-sounds respectively, the discrimination circuit employing the ECG signal to generate the stepping signal applied to the valve control circuit, the improvement comprising:

means within said discrimination circuit for encoding said output data signal into a serial digital pulse-width modulated form; and, a portable magnetic tape recorder connected to said discrimination circuit for recording the encoded output data signal, and having means for combining the ECG signal and the encoded output data signal into a combined signal and for recording the combined signal on a single track in a magnetic tape to preserve the time relationship between the ECG signal and the blood pressure information represented by the output data signal.

8. The improvement of claim 7 further comprising:
a magnetic tape playback unit for playing back said magnetic tape at a faster speed than that at which it was recorded, to produce a playback electrical signal representative of said combined signal;

a data decoder connected to said magnetic tape playback unit and responsive to said combined signal to separate said ECG signal from said output data signal; and, a heart rate trend computer connected to said data decoder and responsive to said ECG signal to produce a heart rate signal representative of the patient's heart rate.

9. The improvement of claim 8 further comprising:

plotter means responsive to said output data signal produced by said data decoder and to said heart rate signal produced by said heart rate trend computer to produce on a common chart representations of both said output data signal and said heart rate signal.

10. The improvement of claim 8 further comprising:

printer means responsive to said output data signal produced by said data decoder for printing numerical symbols representing measured values of the patient's blood pressure.

11. The improvement of claim 7 wherein said portable magnetic tape recorder also simultaneously records on the common magnetic tape an event marker signal initiated by the patient and generated by said portable magnetic tape recorder.

12. The improvement of claim 7 wherein said portable magnetic tape recorder generates an event marker signal under control of the patient and wherein said means for combining combines the event marker signal with the ECG signal and the output data signal, and wherein the combined signal is recorded on a single track on said magnetic tape.

13. In an apparatus for monitoring a patient's blood pressure by the auscultatory method, of the type including an inflatable cuff for affixation to the patient, a source of fluid under pressure for inflating the cuff to an initial inflation pressure during an initial phase of each cycle of operation in response to an applied inflation signal, and thereafter for remaining sealed off from the cuff during the remainder of each cycle of operation, further including a pressure transducer for sensing the pressure of the fluid in the cuff and for generating a pressure signal representative of the pressure, further including a valve connected to the cuff and having a normal first state in which it vents the cuff to a region of lower pressure, and alterable by applied control signals to a second state in which it connects the cuff to the source of fluid, further including a K-sound transducer positioned on the patient in relation to the inflatable cuff for sensing the patient's K-sounds and for generating a K-sound signal representative of the K-sounds, further including a pair of ECG electrodes for sensing the patient's electrocardial potentials and for providing an ECG signal representative thereof, and further including a discrimination circuit responsive to the K-sound signal and to the ECG signal for identifying the first and last of the K-sounds sensed by the K-sound transducer in each cycle of operation and responsive to the pressure signal for producing an output data signal representing the systolic and diastolic pressures sensed by the pressure transducer at the time of occurrence within each cycle of operation of the first and last K-sounds respectively, the discrimination circuit employing the ECG signal to generate the stepping signal applied to the valve control circuit, the improvement comprising in combination:

circuit means, within said discrimination circuit, which upon detecting the occurrence of a K-sound within a limited defined time interval after the end of the initial inflation phase of a cycle, generates a signal for application to the valve control circuit, said valve control circuit including means responsive to said signal for terminating the measurement cycle, for augmenting the initial inflation pressure and for generating an inflation signal to increase the cuff pressure to an augmented initial inflation pressure.

14. The improvement of claim 13 wherein said circuit means, upon failing to detect a K-sound within a limited defined time interval after the end of the initial inflation phase of a cycle, generates a signal for application to the valve control circuit, said valve control circuit including means responsive to said signal for decreasing the initial inflation pressure for the next cycle of operation.

15. A method for repeatedly measuring a patient's systolic blood pressure by an auscultatory method, wherein in each measurement cycle an inflatable cuff fixed to the patient is inflated to an initial inflation pressure and thereafter in each measurement cycle the cuff pressure is gradually reduced so that the K-sounds can be heard, the cuff pressure at the onset of the K-sounds being indicative of the systolic blood pressure and the cuff pressure at the cessation of the K-sounds being indicative of the diastolic blood pressure, said method comprising the steps of:

(a) inflating the cuff, at the beginning of the first cycle to a preset initial inflation pressure;

(b) determining whether or not K-sounds are heard within a limited defined time interval after the cuff has been inflated and proceeding to step (c) if K-sounds were heard within the interval and to step d) if K-sounds were not heard within the interval;

(c) increasing the cuff pressure to a value greater than the preset initial inflation pressure and repeating step (b);

(d) measuring and storing the systolic and diastolic blood pressures;

(e) incrementing the stored systolic blood pressure measurement by a predetermined increment to obtain the initial inflation pressure for the next measurement cycle;

(f) inflating the cuff at the beginning of the next measurement cycle to the initial inflation pressure determined in step (e) and repeating step (b).

16. The method of claim 15 wherein step (d) further comprises the step of:

producing an abrupt decrease of the cuff pressure by a constant predetermined decrement following each of the patient's heartbeats, whereby over an extended time interval the cuff pressure decreases through a series of steps of constant magnitude paced by the patient's heartbeats from an initial pressure greater than the patient's systolic blood pressure to a pressure less than the patient's diastolic blood pressure.

17. The method of claim 16 further comprising the preparatory step of:

sensing the patient's heartbeats from an ECG signal produced by the patient.

18. The method of claim 17 further comprising the step of:

recording the ECG signal in analog form and the blood pressure signals on a single track of a magnetic tape by means of a portable tape recorder affixed to the patient, the intermittent blood pressure signals being interspersed between successive segments of the ECG signal to preserve the time relationship between the signals.

19. The method of claim 18 further comprising the subsequent steps of:
playing back the magnetic tape at a faster rate than that at which it was recorded, to produce a combined signal representing both the ECG signal and the blood pressure signals;
separating the combined signal into components separately representing the ECG signal and the blood pressure signals.

20. The method of claim 19 further comprising the subsequent step of:
producing a heart rate signal from the ECG signal.

21. The method of claim 20 further comprising the subsequent step of:
plotting both the blood pressure signals and the heart rate signal versus time on the same chart.

22. The method of claim 20 further comprising the subsequent steps of:
plotting the heart rate signal versus time on a chart and printing numerical symbols on the chart representing the blood pressure measurements.

23. A portable apparatus for long-term ambulatory monitoring and recording of a patient's systolic and diastolic blood pressure by the auscultatory method, requiring no intervention by the patient, and apparatus for playing back and analyzing the recorded blood pressure data, comprising in combination:
an inflatable cuff affixable to the patient;
a source of fluid under pressure for inflating said cuff to an initial inflation pressure greater than the patient's systolic blood pressure during an initial phase of each cycle of operation in response to an applied inflation signal, and thereafter for remaining sealed off from the cuff during the remainder of each cycle of operation;
a pressure transducer for sensing the pressure of the fluid in said cuff and for generating a pressure signal representative of the pressure;
a valve connected to the cuff and having a normal first state in which it vents said cuff to a region of lower pressure, and alterable by applied control signals to a second state in which it connects said cuff to said source of fluid;
a valve control circuit connected to said valve and generating the control signals applied to said valve to selectively control its state in response to a stored initial inflation pressure signal stored in said valve control circuit and to the pressure signal generated by said pressure transducer to cause said cuff to be inflated to the stored initial inflation pressure during the initial phase of each cycle of operation, the initial inflation pressure signal for the first cycle of operation being preset and the initial inflation pressure signal for each subsequent cycle of operation being determined by said valve control circuit from the greatest pressure measured by said portable apparatus in the immediately preceding cycle of operation and retained in storage by said valve control circuit, said valve control circuit responding to stepping signals generated and applied after the initial pressure inflation phase of each cycle of operation to initiate the control signals applied to said valve to selectively and intermittently vent said cuff to a region of lower pressure momentarily producing an abrupt decrease of the cuff pressure by a constant predetermined decrement upon the occurrence of each of said stepping signals until the cuff pressure has been reduced through a series of constant pressure decrements from the initial inflation pressure greater than the patient's systolic blood pressure to a final cuff pressure less than the patient's diastolic blood pressure;
a K-sound transducer positioned on the patient in relation to said inflatable cuff for sensing the patient's K-sounds during the intervals when the cuff pressure is constant between successive pressure decrements and for generating a K-sound signal representative of the K-sounds;
an ECG electrode for sensing the patient's electrocardial potentials and for providing an ECG signal representative thereof;
a discrimination circuit responsive to the K-sound signal for identifying the first and last of the K-sounds sensed by said K-sound transducer in each cycle of operation and responsive to the pressure signal for producing an output data signal representing the systolic and diastolic pressures sensed by said pressure transducer at the time of occurrence within each cycle of operation of the first and last K-sounds respectively, said discrimination circuit connected to said valve control circuit and producing the stepping signals and applying the stepping signals to said valve control circuit;
said discrimination circuit responsive to the ECG signal to generate the stepping signal applied to said valve control circuit;
said discrimination circuit further comprising means for encoding said output data signal into a serial digital pulse-width modulated form; and,
a portable magnetic tape recorder connected to said discrimination circuit for recording the encoded output data signal, and having means for combining the ECG signal and the encoded output data signal into a combined signal and for recording the combined signal on a single track in a magnetic tape to preserve the time relationship between the ECG signal and the blood pressure information represented by the output data signal.

24. The apparatus of claim 23 wherein said means for combining further comprises multiplexer means.

25. The apparatus of claim 23 further comprising:
a magnetic tape playback unit for playing back said magnetic tape at a faster speed than that at which it was recorded, to produce a playback electrical signal representative of said combined signal;
a data decoder connected to said magnetic tape playback unit and responsive to said combined signal to separate said ECG signal from said output data signal; and,
a heart rate trend computer connected to said data decoder and responsive to said ECG signal to produce a heart rate signal representative of the patient's heart rate.

26. The apparatus of claim 25 further comprising;
plotter means responsive to said output data signal produced by said data decoder and to said heart rate signal produced by said heart rate trend computer to produce on a common chart representations of both said output data signal and said heart rate signal.

27. The apparatus of claim 23 wherein an event marker signal initiated by the patient and generated by said portable magnetic tape recorder is also recorded on said magnetic tape.

28. The apparatus of claim 23 wherein said portable magnetic tape recorder generates an even marker signal under control of the patient and wherein said means for combining combines the event marker signal with the ECG signal and the output data signal and wherein said combined signal recorded on a single track on said magnetic tape includes an event marker signal.

29. The apparatus of claim 23 wherein said discrimination circuit includes means for determining when the patient's R-waves can be recognized in said ECG signal, and when the R-waves can be recognized said discrimination circuit generates and applies to said valve control circuit a stepping signal in timed relation to each R-wave, whereby the cuff pressure is reduced in a stepwise manner, the successive decrements of pressure being paced by successive R-waves.

30. The apparatus of claim 29 wherein said means determines when the patient's R-waves can be recognized in said ECG signal, and when the R-waves cannot be recognized said discrimination circuit generates and applies to said valve control circuit stepping signals having a constant repetition frequency, whereby the cuff pressure is reduced in a stepwise manner, the successive decrements of pressure being equally spaced in time.

31. The apparatus of claim 23 wherein said discrimination circuit including means for determining when the patient's R-waves can be recognized in said ECG signal, and if the R-waves cannot be recognized said discrimination circuit generates and applies to said valve control circuit stepping signals having a constant repetition frequency, whereby the cuff pressure is reduced in a stepwise manner, the successive decrements of pressure being equally spaced in time.

32. The apparatus of claim 23 wherein said discrimination circuit, upon detecting the occurrence of a K-sound within a limited defined time interval after the end of the initial inflation phase of a cycle, generates a signal for application to said valve control circuit, said valve control circuit including means responsive to said signal for terminating the measurement cycle, for augmenting the stored initial inflation pressure signal by a predetermined increment and for generating an inflation signal to increase the cuff pressure to the pressure represented by the augmented initial inflation pressure signal.

* * * * *